United States Patent
Fichtner et al.

(10) Patent No.: US 10,294,245 B2
(45) Date of Patent: May 21, 2019

(54) HIGH PERFORMANCE ORGANIC ELECTRODES FOR SECONDARY BATTERIES

(71) Applicant: Karlsruher Institut für Technologie, Karlsruhe (DE)

(72) Inventors: Maximilian Fichtner, Oftersheim (DE); Zhirong Zhao-Karger, Karlsruhe (DE); Ping Gao, Ulm (DE); Zhi Chen, Eggenstein-Leopoldshafen (DE); Mario Ruben, Strasbourg (FR)

(73) Assignee: Karlsruher Institut für Technologie, Karlsruhe (DE)

( * ) Notice: Subject to any disclaimer, the term of this patent is extended or adjusted under 35 U.S.C. 154(b) by 0 days.

(21) Appl. No.: 15/425,462

(22) Filed: Feb. 6, 2017

(65) Prior Publication Data

US 2017/0226134 A1    Aug. 10, 2017

(30) Foreign Application Priority Data

Feb. 8, 2016  (EP) .................................. 16000312

(51) Int. Cl.
  *C07F 1/08*  (2006.01)
  *H01M 4/62*  (2006.01)
  *H01M 4/60*  (2006.01)

(52) U.S. Cl.
  CPC ............... *C07F 1/08* (2013.01); *H01M 4/60* (2013.01); *H01M 4/622* (2013.01)

(58) Field of Classification Search
  None
  See application file for complete search history.

(56) References Cited

U.S. PATENT DOCUMENTS

| 4,550,067 A | 10/1985 | Horiba et al. |
| 2008/0299456 A1 | 12/2008 | Shiga et al. |

FOREIGN PATENT DOCUMENTS

| CN | 101333437 A | 12/2008 |
| JP | 2013-182862 A | 9/2013 |

(Continued)

OTHER PUBLICATIONS

JP2013182862 English translation. Hayashi et al. Japan. Sep. 2013. (Year: 2013).*

(Continued)

*Primary Examiner* — Jonathan G Leong
*Assistant Examiner* — Christopher P Domone
(74) *Attorney, Agent, or Firm* — McDonnell Boehnen Hulbert & Berghoff LLP

(57) ABSTRACT

The present disclosure relates to a compound of general Formula (1) which can be used as an electrode material, an electrode comprising said compound, and a battery cell comprising at least one of said electrode.

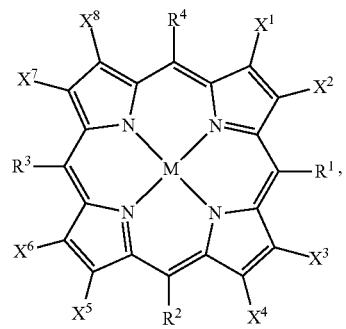

(Formula (1))

wherein M is selected from the group consisting of a transition metal ion, preferably selected from the group consisting of Ti, Cr, Mn, Fe, Co, Ni, Cu, Zn, Zr, Mo, Ru, Rh, Pd, Ag, W, Re, Os, Ir, Pt, and Au, an alkaline earth metal ion, preferably selected from the group consisting of Mg and Ca, a p-block element ion, preferably selected from the group consisting of B, Al, Ga, In, Si, Ge, Sn, Pb, As, Sb, Bi, Se, and (Continued)

Te, and a lanthanide ion, preferably selected from the group consisting of La, Ce, Sm, and Eu, $R^1$ to $R^4$ and $X^1$ to $X^8$ are each independently selected from the group consisting of a hydrogen atom, an alkyl group, an alkenyl group, an alkynyl group, an aryl group, a heteroaryl group, a halogen atom, $-NZ^1Z^2$, $-NO_2$, $-CN$, $-OZ^3$, $-C(O)Z^4$, $-C(O)NZ^5Z^6$, and $-COOZ^7$, wherein at least one of $R^1$ to $R^4$ is an alkynyl group, $Z^1$ to $Z^7$ are each independently selected from a hydrogen atom, an alkyl group, an alkenyl group, an alkynyl group, an aryl group, a heteroaryl group, and a halogen atom, and wherein the alkyl groups, the alkenyl groups, the alkynyl groups, the aryl groups, and the heteroaryl groups are each independently substituted or unsubstituted.

11 Claims, 22 Drawing Sheets

(56) References Cited

FOREIGN PATENT DOCUMENTS

| JP | 2013182862 | * | 9/2013 |
| JP | 2015-15454 | A | 1/2015 |

OTHER PUBLICATIONS

LeCours et al. "Synthesis Transient Adsorption, and Transient Resonance Raman Spectroscopy of Novel Electron Donor". J Am Chem Soc 1997, 119, 12578-12589. (Year: 1997).*

Di Natale et al. "The exploitation of metalloporphyrins as chemically interactive material in chemical sensors". Materials Sceience & Engineering C 5 (1998) p. 209-215. (Year: 1998).*

Ryan, A., et al., "Porphyrin Dimers and Arrays", Eur. J. Org. Chem., vol. 2011(29), Oct. 24, 2011, pp. 5817-5844, doi:10.1002/ejoc.201100642.

Shediac, R., et al., "Singlet and Triplet Excited States of Emissive, Conjugated Bis(porphyrin) Compounds Probed by Optical and EPR Spectroscopic Methods", J. Am. Chem. Soc., Jul. 1, 2000, vol. 122(29), pp. 7017-7033.

Sheridan, M.V., et al., "Covalent Attachment of Porphyrins and Ferrocenes to Electrode Surfaces through Direct Anodic Oxidation of Terminal Ethynyl Groups", Angew. Chem. Int. Ed., Dec. 2, 2013, vol. 52(49), pp. 12897-12900, doi:10.1002/anie.201307453.

Extended European Search Report, received from the European Patent Office, dated Sep. 16, 2016, for European Application No. 16000312.5-1373, pp. 1-16.

LeCours, S.M., et al., "Synthesis, Transient Absorption, and Transient Resonance Raman Spectroscopy of Novel Electron Donor—Acceptor Complexes: [5,15-Bis[4'-nitrophenyl)ethynyl]-10,20-diphenylporphinato]copper(II) and [5-[[4'(Dimethylamino)phenyl]ethynyl]-15-[(4"-nitrophenyl)ethynyl]-10,20-diphenylporphinato]copper(II)", J. Am. Chem. Soc., Dec. 1, 1997, vol. 119(51), pp. 12578-12589.

Japanese Office Action, received from the Japanese Patent Office, dated May 8, 2018, for Japanese Application No. 2017-015491, pp. 1-8.

* cited by examiner (anode)CuDEPP | PP$_{14}$TFSI | Graphite(cathode)

(cell 2)

(anode) CuDEPP | LiPF$_6$ | CuDEPP (cathode)

(cell 3)

HIGH PERFORMANCE ORGANIC ELECTRODES FOR SECONDARY BATTERIES

CROSS-REFERENCE

This application claims priority from European patent application no. 16 000 312.5, filed Feb. 8, 2016, which is incorporated by reference in its entirety.

FIELD

The present disclosure relates to a compound, which can be used as an electrode material, an electrode comprising said compound, and a battery cell comprising at least one of said electrode.

BACKGROUND

Rechargeable lithium ion batteries (LIBs) have been successfully developed over the last two to three decades and widely used to power today's portable electronic devices. The aim at long-term success in electric vehicles and grid-scale renewable energy storage raises great challenges with respect to high energy densities, long cycle lives, good safety and low-costs of the batteries. It is recognized that conventional lithium ion battery systems are approaching their theoretical energy density limits and their lifetime and charging rate must be improved.

Rechargeable batteries based on organic electrode materials are potential alternatives to conventional lithium-ion batteries due to their tunable properties, environmental friendliness, flexibility, good safety, sustainability and relative low cost. The organic molecules can be divided into n-type organic, p-type organic, and bipolar organic molecules, in which the neutral molecule can be either oxidized to the positively charged state or reduced to the negatively charged state.

Different from conventional inorganic electrode materials in LIBs, the battery performance of organic electrodes greatly depends on their molecular structures, which can be desirably tailored by synthesis.

Porphyrins have an aromatic 18 π conjugated system delocalized over 24 core atoms which satisfy Hückel's (4n+2) π-electron rule. Many porphyrins and metalloporphyrins exist naturally and have a wide range of application, e.g. in light harvesting, as a catalyst, or in solar cells. Porphyrins and their derivatives with highly conjugated π-systems are suitable for efficient electron transfer processes due to the minimal structural change of the molecules during the removal or uptake of an electron. 16 π-electron and 20 π-electron "antiaromatic" porphyrins are accessible by the oxidation or reduction of the 18 π-electron systems of aromatic porphyrins and in some cases can be successfully isolated and structurally determined.

However, so far no organic electrode materials had been available which are able to provide batteries having high power, high energy densities as well as very good cyclic stabilities.

SUMMARY

Thus, the technical problem underlying the present disclosure is to provide a compound, which can be used as an "organic" electrode material, as well as a corresponding battery cell having a high power density as well as a superior energy density.

The solution to the above technical problem is achieved by the embodiments characterized in the claims.

The present disclosure relates to a compound which can be used as an electrode material, an electrode comprising said compound, and a battery cell comprising at least one of said electrode.

In particular, the present disclosure relates to a compound of the general Formula (1)

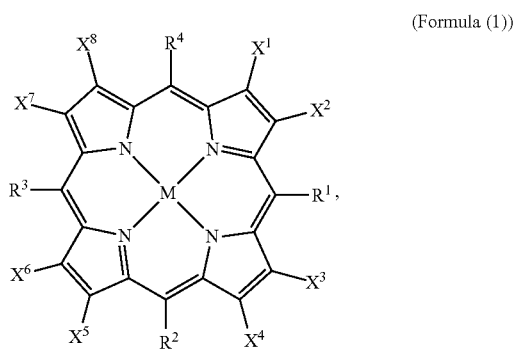

(Formula (1))

wherein M is selected from the group consisting of a transition metal ion, preferably selected from the group consisting of Ti, Cr, Mn, Fe, Co, Ni, Cu, Zn, Zr, Mo, Ru, Rh, Pd, Ag, W, Re, Os, Ir, Pt, and Au, an alkaline earth metal ion, preferably selected from the group consisting of Mg and Ca, a p-block element ion, preferably selected from the group consisting of B, Al, Ga, In, Si, Ge, Sn, Pb, As, Sb, Bi, Se, and Te, and a lanthanide ion, preferably selected from the group consisting of La, Ce, Sm, and Eu, $R^1$ to $R^4$ and $X^1$ to $X^8$ are each independently selected from the group consisting of a hydrogen atom, an alkyl group, an alkenyl group, an alkynyl group, an aryl group, a heteroaryl group, a halogen atom, $-NZ^1Z^2$, $-NO_2$, $-CN$, $-OZ^3$, $-C(O)Z^4$, $-C(O)NZ^5Z^6$, and $-COOZ^7$, wherein at least one of $R^1$ to $R^4$ is an alkynyl group, $Z^1$ to $Z^7$ are each independently selected from a hydrogen atom, an alkyl group, an alkenyl group, an alkynyl group, an aryl group, a heteroaryl group, and a halogen atom, and wherein the alkyl groups, the alkenyl groups, the alkynyl groups, the aryl groups, and the heteroaryl groups are each independently substituted or unsubstituted.

Figure 1:
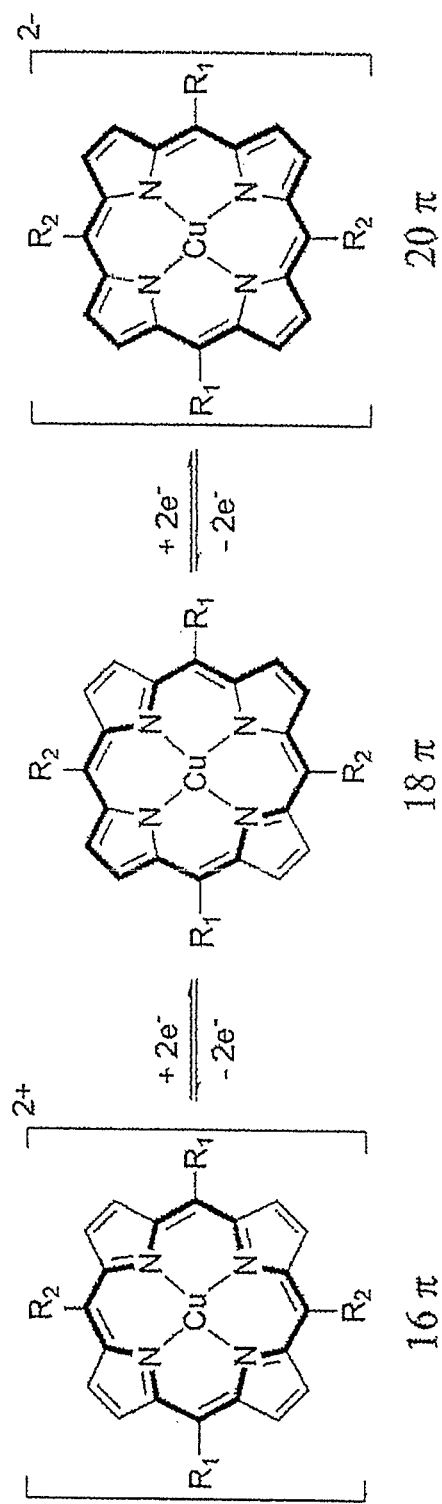
FIG. 1: Schematics of the electron transformations: oxidation and reduction transformations among the 16, 18, 20 π-electrons of the porphyrin core. The bold line denotes each π-conjugation circuit ($R_1$=ethynyl, $R_2$=phenyl (i.e. CuDEPP)).

The present disclosure will be further illustrated in the following examples without being limited thereto.

DETAILED DESCRIPTION

In particular, the present disclosure relates to a compound of the general Formula (1)

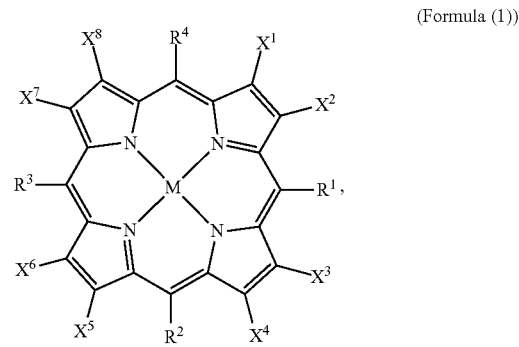

(Formula (1))

wherein M is selected from the group consisting of a transition metal ion, preferably selected from the group consisting of Ti, Cr, Mn, Fe, Co, Ni, Cu, Zn, Zr, Mo, Ru, Rh, Pd, Ag, W, Re, Os, Ir, Pt, and Au, an alkaline earth metal ion, preferably selected from the group consisting of Mg and Ca, a p-block element ion, preferably selected from the group consisting of B, Al, Ga, In, Si, Ge, Sn, Pb, As, Sb, Bi, Se, and Te, and a lanthanide ion, preferably selected from the group consisting of La, Ce, Sm, and Eu, R$^1$ to R$^4$ and X$^1$ to X$^8$ are each independently selected from the group consisting of a hydrogen atom, an alkyl group, an alkenyl group, an alkynyl group, an aryl group, a heteroaryl group, a halogen atom, —NZ$^1$Z$^2$, —NO$_2$, —CN, —OZ$^3$, —C(O)Z$^4$, —C(O)NZ$^5$Z, and —COOZ$^7$, wherein at least one of R$^1$ to R$^4$ is an alkynyl group, Z$^1$ to Z$^7$ are each independently selected from a hydrogen atom, an alkyl group, an alkenyl group, an alkynyl group, an aryl group, a heteroaryl group, and a halogen atom, and wherein the alkyl groups, the alkenyl groups, the alkynyl groups, the aryl groups, and the heteroaryl groups are each independently substituted or unsubstituted.

According to the present disclosure, M is selected from the group consisting of a transition metal ion, preferably selected from the group consisting of Ti, Cr, Mn, Fe, Co, Ni, Cu, Zn, Zr, Mo, Ru, Rh, Pd, Ag, W, Re, Os, Ir, Pt, and Au, an alkaline earth metal ion, preferably selected from the group consisting of Mg and Ca, a p-block element ion, preferably selected from the group consisting of B, Al, Ga, In, Si, Ge, Sn, Pb, As, Sb, Bi, Se, and Te, and a lanthanide ion, preferably selected from the group consisting of La, Ce, Sm, and Eu. Preferably, the ions are in a stable oxidation state (for example Cu(II)). The electron transfer processes of porphyrin complexes depend on the nature of the central metal ions M as well as the axial coordination that may alter the structural, spectroscopic and the redox properties. In a preferred embodiment of the present application, M is Cu(II). Cu(II) porphyrin complexes possess low reactivity at the metal ion and are therefore particularly suitable for the utilization as electrode-active materials in rechargeable batteries, since a redox reaction at the central metal may lead to undesired structural changes in the initial porphyrins and may thus negatively influence the reversibility of the battery.

The commercial available porphyrin complex [5,10,15,20-tetraphenylporphinato]copper(II) (CuTPP) was initially probed as a cathode in a battery system further comprising a Li metal anode and 1 M LiPF$_6$ in a solvent mixture of ethylene carbonate (EC), dimethyl carbonate (DMC), and propylene carbonate (PC) as the electrolyte. However, the battery's performance was not satisfying, probably due to the high solubility of active material in the electrolyte or other inherent limitations of its electrochemical properties.

According to the present disclosure, the introduction of at least one alkynyl, preferably ethynyl, moiety in porphyrins surprisingly results in compounds, which show an excellent battery performance, with storage capacities comparable to those of state-of-the art systems but with charge and discharge rates being comparable to those of capacitors and superior to those of lithium ion batteries, as will be described herein below. Thus, according to the general Formula (1) of the present disclosure, at least one or two of $R^1$ to $R^4$ is/are an alkynyl group. Preferably, at least one or two of $R^1$ to $R^4$ is/are an ethynyl group.

Herein the term "halogen" refers particularly to fluorine atoms, chlorine atoms, bromine atoms, and iodine atoms. The term "alkyl group" refers particularly to a branched or linear alkyl group having 1 to 20, preferably 1 to 12, more preferably 1 to 6, and most preferably 1 to 4 carbon atoms, which can be substituted or unsubstituted. The term "alkenyl group" refers particularly to a branched or linear alkenyl group having 2 to 20, preferably 2 to 12, more preferably 2 to 6, and most preferably 2 to 4 carbon atoms, which can be substituted or unsubstituted. The term "alkynyl group" refers particularly to a branched or linear alkynyl group having 2 to 20, preferably 2 to 12, more preferably 2 to 6, more preferably 2 to 4 carbon atoms, and most preferably 2 carbon atoms (i.e. an ethynyl group), which can be substituted or unsubstituted. The term "aryl group" refers particularly to an aryl group consisting of 1 to 6, preferably 1 to 4, more preferably 1 to 3 rings, and most preferably 1 ring, which can be substituted or unsubstituted. Examples of aryl groups represent phenyl groups, anthracenyl or naphthyl groups. The term "heteroaryl group" refers particularly to a heteroaryl group consisting of 1 to 6, preferably 1 to 4, more preferably 1 to 3 rings, which can be substituted or unsubstituted. Examples of heteroaryl groups represent pyridyl groups, pyrimidinyl groups, thienyl groups, furyl groups or pyrrolyl groups.

According to the present disclosure, the ethynyl groups, the phenyl groups, the alkyl groups, the alkenyl groups, the alkynyl groups, the aryl groups and the heteroaryl groups may be substituted or unsubstituted. The potential substituents are not specifically limited. Accordingly, instead of hydrogen atoms any substituent known in the prior art can be bonded to the further positions of the corresponding groups. For example, the potential substituents may be selected from the group consisting of an alkyl group, an alkenyl group, an alkynyl group, an aryl group, a heteroaryl group, a halogen atom, $-NZ^1Z^2$, $-NO_2$, $-CN$, $-OZ^3$, $-C(O)Z^4$, $-C(O)NZ^5Z^6$, and $-COOZ^7$, wherein $Z^1$ to $Z^7$ are each independently selected from a hydrogen atom, an alkyl group, an alkenyl group, an alkynyl group, an aryl group, a heteroaryl group, and a halogen atom. Most preferably, the ethynyl groups, the phenyl groups, the alkyl groups, the alkenyl groups, the alkynyl groups, the aryl groups and the heteroaryl groups are unsubstituted.

In a preferred embodiment of the compound according to the present disclosure, $R^1$ and $R^3$ are each an alkynyl group. More preferably, $R^1$ and $R^3$ are each an ethynyl group.

Preferably, $R^2$ and $R^4$ are each an aryl group. More preferably, $R^2$ and $R^4$ are each a phenyl group.

In a preferred embodiment of the compound according to the present disclosure, the compound of Formula (1) is [5,15-bis(ethynyl)-10,20-diphenylporphinato]copper(II) (CuDEPP, cf. Formula (2)), meaning that $R^1$ and $R^3$ are each an unsubstituted ethynyl group, $R^2$ and $R^4$ are each an unsubstituted phenyl group, and $X^1$ to $X^8$ are each a hydrogen atom.

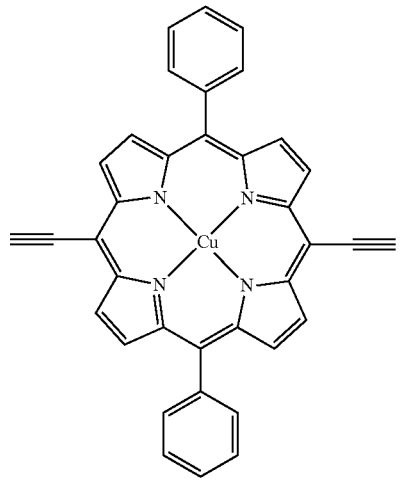

(Formula (2))

[5,15-Bis(ethynyl)-10,20-diphenylporphinato]copper(II) (CuDEPP) bearing two meso ethynyl groups can be successfully synthesized in a moderate overall yield and can be characterized by means of matrix-assisted laser desorption ionization time-of-flight mass spectroscopy (MALDI-TOF-MS), ultraviolet-visible spectroscopy (UV-vis) and infrared spectroscopy (IR). Notably, the thermogravimetric-differential scanning calorimetric analysis (TGA-DSC) indicates that the CuDEPP molecule is thermally stable up to 250° C. in air, which may be attributed to its highly π-conjugated structure and aromatic character.

Moreover, CuDEPP has a relatively low solubility in the applied electrolytes when compared to CuTPP, which is beneficial for battery applications. On the other hand, the low solubility in common organic solvents such as dichloromethane ($CH_2Cl_2$) and acetonitrile ($CH_3CN$) prohibits the electrochemical analysis of CuDEPP by cyclic voltammetry (CV) in a solution condition. Based on the reported redox chemistry of the analogue compound CuTPP, a reversible two-electron oxidation and a two-electron reduction can be proposed for CuDEPP bearing 18 π-electrons, forming a dicationic species (CuDEPP$^{2+}$, 16 π-electrons) and a dianionic species (CuDEPP$^{2-}$, 20 w-electrons), respectively (cf. FIG. 1).

In a further aspect, the present disclosure relates to the use of the compound according to the present disclosure as an electrode material in a battery, preferably secondary battery. The above statements and definitions analogously apply to this aspect of the present disclosure. By using the compound according to the present disclosure as an electrode material, it is advantageously possible to produce electrodes with superior electrochemical properties, which can be used both as a cathode and an anode. Thus, even all-organic batteries can be provided by using the compound according to the present disclosure as an electrode material.

In a further aspect, the present disclosure relates to an electrode comprising the compound according to the present disclosure. The above statements and definitions analogously apply to this aspect of the present disclosure.

The content of the compound according to the present disclosure in the electrode is not specifically limited. Accordingly, the electrode may consist exclusively of the compound of the present disclosure or may also comprise or consist of further electrode materials. Thus, in a preferred embodiment of the present disclosure, the content (by weight) of the compound according to the present disclosure is from 20% to 100%, based on the total weight of the electrode. More preferably, the content of the compound according to the present disclosure is from 20% to 95%, even more preferably from 30% to 80%, from 40% to 75%, from 45% to 70%, and most preferably from 50% to 65%, based on the total weight of the electrode.

The potential further electrode materials apart from the compound of the present disclosure are not specifically limited. Therefore, all kinds of electrode materials known in the art may be used. For example, the electrode may further comprise or consist of binders and/or electrically conductive additives, as e.g. carbon black, carbon nanotubes, carton nanofibers, graphite, graphene, and graphene oxide. In a preferred embodiment, the electrode of the present disclosure comprises the compound according to the present disclosure, a binder, and carbon black. More preferably, the electrode according to the present disclosure consists of the compound according to the present disclosure, a binder, and carbon black.

In a preferred embodiment of the present disclosure, the content (by weight) of the binder in the electrode according to the present disclosure is from 0% to 40%, based on the total weight of the electrode. More preferably, the content of the binder is from 0% to 30%, even more preferably from 2% to 25%, from 3% to 20%, from 4% to 15%, and most preferably from 5% to 12%, based on the total weight of the electrode.

The possible binders are not specially limited. Thus, any binder known in the art can potentially be present in the electrode according to the present disclosure. For example, the binder, when present, can be selected from the group consisting of polyvinylidene fluoride (PVDF), polyvinylidene fluoride-co-hexafluoropropene (PVDF-HFP), sodium carboxymethyl cellulose (CMC), polyvinylpyrrolidone (PVP), poly(ethyleneoxide) (PEO), polytetrafluoroethylene (PTFE), and poly(acrylic acid) (PAA). Preferably, the binder is selected from the group consisting of polyvinylidene fluoride (PVDF), polyvinylidene fluoride-co-hexafluoropropene (PVDF-HFP), sodium carboxymethyl cellulose (CMC), and polytetrafluorethylene (PTFE). Most preferably, the binder is polyvinylidene fluoride (PVDF). Polyvinylidene fluoride (PVDF) provides advantages in electrode processing, for example in terms of versatility, environmental impact and safety.

In a preferred embodiment of the present disclosure, the content (by weight) of electrically conductive additives in the electrode according to the present disclosure is from 0% to 80%, based on the total weight of the electrode. More preferably, the content of electrically conductive additives is from 10% to 70%, even more preferably from 20% to 65%, from 25% to 60%, from 30% to 50%, and most preferably from 35% to 45%, based on the total weight of the electrode. A content of electrically conductive additives falling out of the above-identified range may lead to a lower reversible capacity.

In a further aspect, the present disclosure relates to a battery cell comprising at least one electrode according to the present disclosure. The above statements and definitions analogously apply to this aspect of the present disclosure.

The electrolyte used in the battery cell is not specifically limited. Thus, any electrolyte known in the art can be used in the battery cell according to the present disclosure. For example, the electrolyte can be selected from the group consisting of $LiPF_6$, 1-butyl-1-methylpiperidinium bis(trifluoromethylsulfonyl)imide ($PP_{14}TFSI$), lithium perchlorate ($LiClO_4$), lithium trifluoromethane sulfonate ($LiCF_3SO_3$), lithium bis(trifluoromethanesulfonyl)imide (LiTFSI), lithium bis(perfluoroethylsulfonyl)imide ($LiN(CF_3CF_2SO_2)_2$), lithium tetrafluoroborate ($LiBF_4$), lithium bis(oxalato) borate ($LiB(C_2O_4)_2$), sodium hexafluorophosphate ($NaPF_6$), sodium perchlorate ($NaClO_4$), N-methyl-N-propylpyrrolidinium bis(trifluoromethanesulfonyl)imide ($PP_{13}TFSI$) and ionic liquids, which consist of organic cations such as 1-alkyl-3-methylimidazolium, 1-alkylpyridinium, N-methyl-N-alkylpyrrolidinium, ammonium, and phosphonium, and anions such as halides, tetrafluoroborate, hexafluorophosphate, bistriflimide, triflate, or tosylate. Preferably, the electrolyte is selected from the group consisting of $LiPF_6$, $PP_{14}TFSI$, $LiClO_4$, LiTFSI, $LiN(CF_3CF_2SO_2)_2$, $LiB(C_2O_4)_2$, $NaPF_6$, $NaClO_4$, and $PP_{13}TFSI$. Most preferably, the electrolyte is selected from the group consisting of $LiPF_6$ and $PP_{14}TFSI$.

The electrolyte may be dissolved in a solvent or a solvent mixture. Solvents for electrolyte solutions are known in the art. For example, the electrolyte can be dissolved in one or more solvents selected from the group consisting of ethylene carbonate (EC), dimethyl carbonate (DMC), propylene carbonate (PC), 1,3-dioxolane (DOL), 1,2-dimethoxyethane (DME), γ-butyrolactone, acetonitrile, and glymes. Preferably, the electrolyte is dissolved in one or more solvents selected from the group consisting of ethylene carbonate (EC), dimethyl carbonate (DMC), propylene carbonate (PC), and γ-butyrolactone. Most preferably, the electrolyte is dissolved in a solvent mixture consisting of ethylene carbonate (EC), dimethyl carbonate (DMC) and propylene carbonate (PC).

The mixture ratio of the one or more solvents for dissolving the electrolyte, when present, is not specifically limited. For example, when ethylene carbonate (EC), dimethyl carbonate (DMC) and propylene carbonate (PC) are used as a solvent mixture, 10 to 80 parts by volume of ethylene carbonate (EC), preferably 20 to 60 parts by volume, and most preferably 30 to 50 parts by volume, may be mixed with 10 to 80 parts by volume of dimethyl carbonate (DMC), preferably 20 to 60 parts by volume, and most preferably 30 to 50 parts by volume, as well as 10 to 80 parts by volume of propylene carbonate (PC), preferably 10 to 60 parts by volume, and most preferably 15 to 40 parts by volume, based on a total volume of the solvent mixture of 100 parts.

When dissolved, the concentration of the electrolyte in the solvent or the solvent mixture is not specifically limited. Preferably, the concentration of the electrolyte in the solvent or the solvent mixture is from 0.01 to 5 M, more preferably from 0.1 to 4 M, from 0.2 to 3 M, from 0.4 to 2 M, from 0.6 to 1.5 M, and most preferably from 0.8 to 1.2 M.

As already stated above, an electrode according to the present disclosure which comprises the compound according to the present disclosure can advantageously be used as a cathode and/or an anode in a battery cell.

Figure 2:
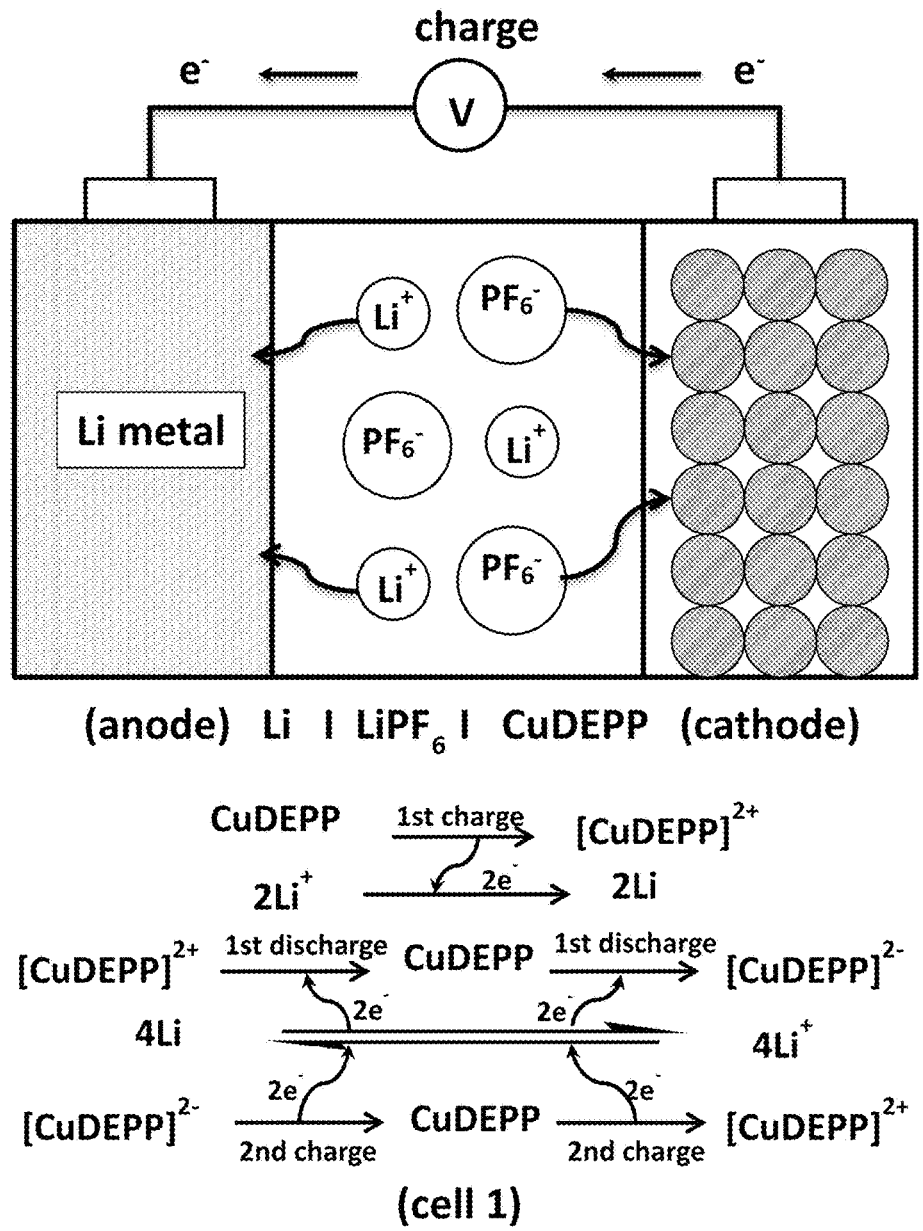
FIG. 2: Cell system wherein the electrode according to the present disclosure is used as a cathode, and the corresponding schemes of the electron transformations between the cathode and the anode in the charge and discharge process.

Thus, according to one embodiment of the battery cell according to the present disclosure, the battery cell comprises one electrode according to the present disclosure, wherein said electrode is operated/functions as a cathode. One example of a corresponding battery cell is depicted in FIG. 2. The anode of the battery cell according to this embodiment is not specifically limited. Thus any anode known in the prior art can be used. For example, the anode can be selected from the group consisting of a Li electrode, as for example a Li foil, a $Li_4Ti_5O_{12}$ electrode, a $Li_{4.4}Sn$ electrode, a $Li_{4.4}Si$ electrode, a sodium (Na) electrode, a potassium (K) electrode, a magnesium (Mg) electrode, and a calcium (Ca) electrode. Preferably, the anode is a lithium electrode. Most preferably, the anode is a Li foil. The electrolyte used for the battery cell of this embodiment is preferably $LiPF_6$. This electrolyte has a high chemical stability and good electrochemical properties. Advantageously, a battery cell according to this embodiment possesses an excellent specific energy density. For example, a battery cell according to this embodiment possesses a specific energy density of at least 345 Wh/kg, preferably of at least 375 Wh/kg, at least 396 Wh/kg, at least 429 Wh/kg, and most preferably of at least 555 Wh/kg. Moreover, a battery cell according to this embodiment has an excellent specific power density. For example, the specific power density of such a battery cell is at least 590 W/kg, preferably at least 2900 W/kg, at least 5900 W/kg, at least 18000 W/kg, and most preferably at least 29500 W/kg.

Furthermore, a battery cell comprising the electrode according to the present disclosure as a cathode advantageously possesses an excellent long-term cycle life and an outstanding rate performance. Remarkably, even at high current densities of e.g. 10 A $g^{-1}$, the electrode according to the present disclosure can still deliver a stable reversible discharge capacity (e.g. 115 mAh $g^{-1}$ with an average output voltage of 3 V (vs Li/Li$^+$), obtained within 42 seconds with a coulombic efficiency of 99.5%), which demonstrates its excellent electrochemical performance. Moreover, a capacity retention of 85% after 2000 cycles and of 60% after 8000 cycles can for example be obtained at a current rate of 4 A $g^{-1}$. Preferably, a first charging process is conducted when using a battery system which comprises the electrode of the present disclosure as a cathode, since said first charging process results in a superior battery performance.

Figure 3:
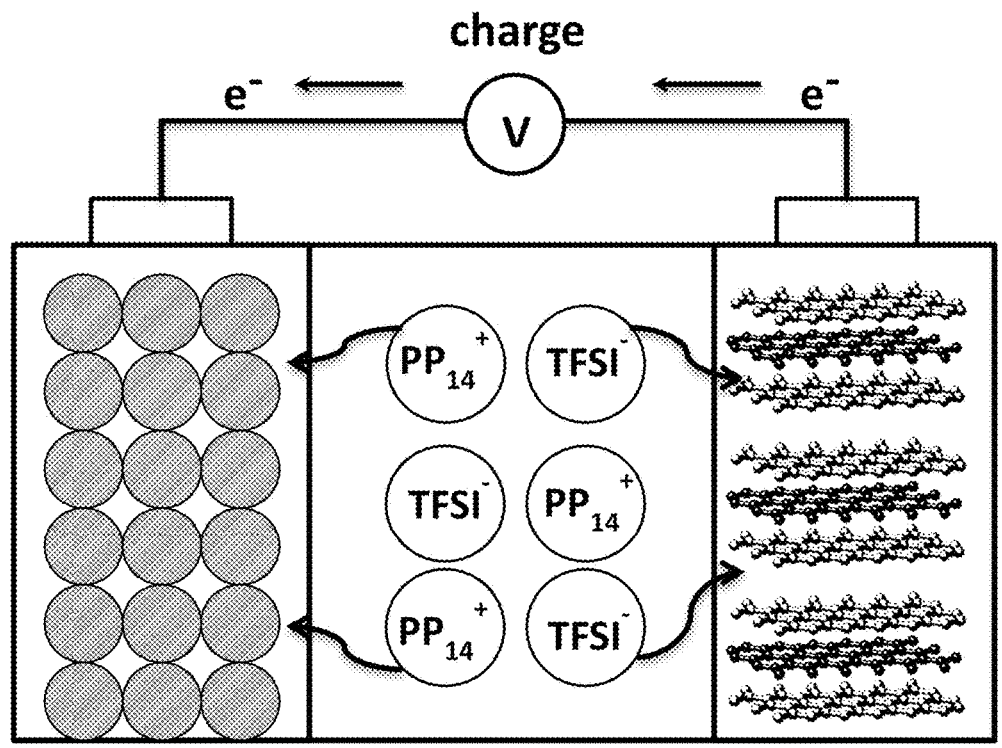
FIG. 3: Cell system wherein the electrode according to the present disclosure is used as an anode, and the corresponding schemes of the electron transformations between the cathode and the anode in the charge and discharge process.
Figure 3:
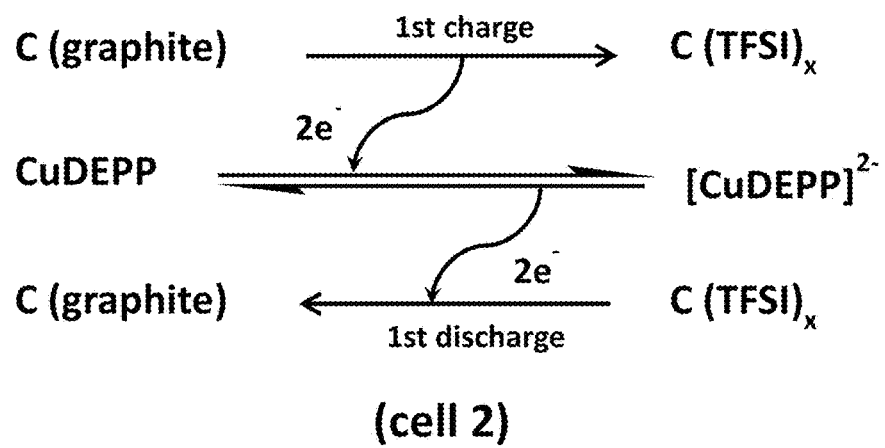

According to another embodiment of the battery according to the present disclosure, the battery cell comprises one electrode according to the present disclosure, wherein said electrode is operated/functions as an anode. One example of a corresponding battery cell is depicted in FIG. 3.

The cathode of the battery cell according to this embodiment is not specifically limited. Thus any cathode known in the prior art can be used. Preferably, cathode materials with layered structures are used. Accordingly, the cathode is preferably selected from the group consisting of a graphite electrode, a graphene electrode, a graphene oxide electrode, and a $MoS_2$ electrode. More preferably, the cathode is selected from the group consisting of a graphite electrode, a graphene electrode, and a graphene oxide electrode. Most preferably, the cathode is a graphite electrode.

The electrolyte used for the battery cell of this embodiment is preferably 1-butyl-1-methylpiperidinium bis(trifluoromethylsulfonyl)imide ($PP_{14}TFSI$). $PP_{14}TFSI$ has a high dielectric constant and ionic conductivity and it is safe for battery application due to its high chemical and thermal stability as well as non-toxic properties.

Upon charging, the compound according to the present disclosure, as e.g. CuDEPP, accepts electrons from the external circuit and is reduced to e.g. a CuDEPP$^{2-}$ species. In parallel, when e.g. $PP_{14}TFSI$ is used as the electrolyte and e.g. graphite is used as the cathode, TFSI$^-$ anions from the electrolyte can be intercalated into the graphite cathode. In this case, $PP_{14}^+$ cations from the electrolyte compensate the negative charge of CuDEPP$^{2-}$ anions. During reverse discharge, the TFSI$^-$ anions are de-intercalated from the graphite cathode, while CuDEPP$^{2-}$ anions of the anode release electrons to the external circuit and are oxidized to the neutral state.

Advantageously, a battery cell according to this embodiment possesses a good specific energy density. For example, a battery cell according to this embodiment possesses a specific energy density of at least 40 Wh/kg, preferably of at least 60 Wh/kg, at least 80 Wh/kg, at least 100 Wh/kg, and most preferably of at least 120 Wh/kg.

Moreover, a battery cell according to this embodiment has an excellent specific power density. For example, the specific power density of such a battery cell is at least 1100 W/kg, preferably at least 2000 W/kg, at least 3000 W/kg, at least 6000 W/kg, and most preferably at least 14000 W/kg.

A battery cell comprising the electrode according to the present disclosure as an anode can advantageously deliver a high specific power of e.g. 14 kW $kg^{-1}$ at a high current density of 10 A $g^{-1}$ (discharge capacity of 32 mAh $g^{-1}$ within 12 seconds). Such values have only been possible with electrochemical capacitors so far.

Apart from the two above-described embodiments, the bipolar redox reactivity of the compound according to the present application enables the construction of an all-organic rechargeable battery. Thus, according to another embodiment of the present disclosure, the battery cell comprises two electrodes according to the present disclosure, wherein one of the two electrodes is operated as a cathode and the other electrode is operated as an anode.

Figure 4:
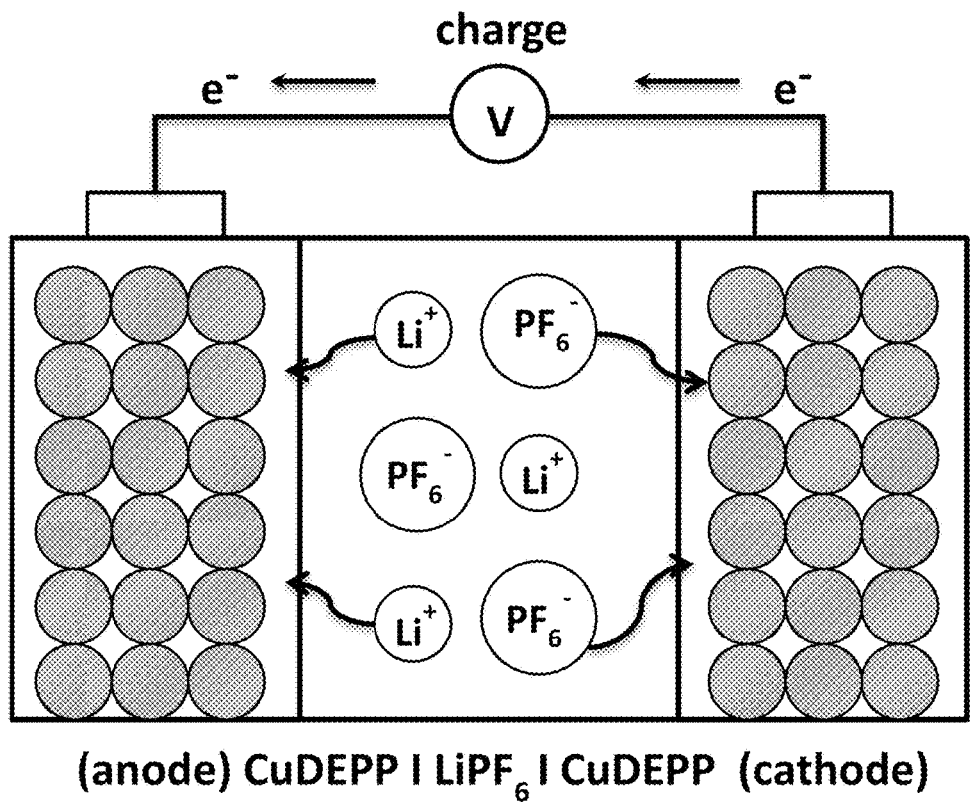
FIG. 4: Cell system wherein the electrode according to the present disclosure is used as a cathode as well as an anode, and the corresponding schemes of the electron transformations between the cathode and the anode in the charge and discharge process.
Figure 4:
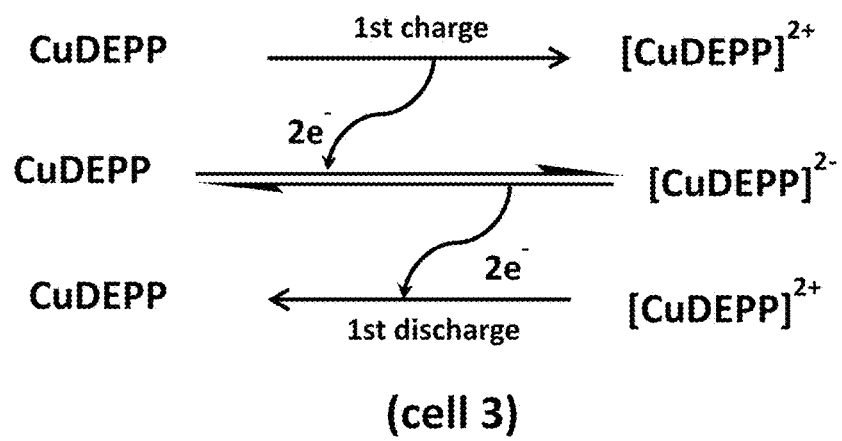

The working mechanism of such an all-organic battery is schematically illustrated in FIG. 4 in the form of a CuDEPP/$LiPF_6$/CuDEPP cell. During charging, the CuDEPP anode accepts electrons from an external circuit forming a CuDEPP$^{2-}$ species with Li$^+$ insertion from the electrolyte for the charge balance, while the CuDEPP cathode donates its electrons to an external circuit with $PF_6^-$ insertion for the charge balance. On reverse discharge, the CuDEPP$^{2-}$ dianions in the anode release electrons and are oxidized to the neutral state of CuDEPP, while the CuDEPP$^{2+}$ dications in the cathode uptake electrons and are reduced to the neutral state of CuDEPP. The Li$^+$ and $PF_6^-$ ions from the anode and cathode return to the electrolyte.

The electrolyte used for the battery cell of this embodiment is preferably $LiPF_6$.

Advantageously, a battery cell according to this embodiment possesses an excellent specific energy density. For example, a battery cell according to this embodiment possesses a specific energy density of at least 48 Wh/kg, preferably of at least 60 Wh/kg, at least 80 Wh/kg, at least 120 Wh/kg, and most preferably of at least 150 Wh/kg.

Moreover, a battery cell according to this embodiment has a superb specific power density. For example, the specific power density of such a battery cell is at least 150 W/kg, preferably at least 160 W/kg, at least 200 W/kg, at least 240 W/kg, and most preferably at least 250 W/kg.

The compound according to the present disclosure, as e.g. the aromatic porphyrin complex CuDEPP, has been identified as a novel bipolar redox material enabling diverse rechargeable battery configurations. Different battery systems can be realized by employing said compound as an electrode material. For example, a Li/LiPF$_6$/CuDEPP battery can deliver an initial discharge capacity of 210 mAh g$^{-1}$. With such a battery a capacity retention of approximately 85% and 60% at a high current density of 4 A g$^{-1}$ can be maintained within 2000 and 8000 cycles, respectively, which demonstrates an excellent cyclability with a high average potential of 3.0 V (vs Li). Remarkably, a stable reversible discharge capacity of e.g. 115 mAh g$^{-1}$ can be achieved at a current of 10 A g$^{-1}$ within 42 seconds, offering an outstanding specific power of 29 kW kg$^{-1}$ and a high specific energy density of 345 Wh kg$^{-1}$.

The compound of the present disclosure can also be applied in a lithium free battery as e.g. a CuDEPP/PP$_{14}$TFSI/graphite battery, in which the CuDEPP serves as an anode-active material. In this case, a discharge capacity of e.g. 94 mAh g$^{-1}$ can be obtained at a current density of 1 A g$^{-1}$. Moreover, superb cycling and an excellent rate performance can be achieved.

In an all-organic symmetric configuration, the bipolar redox reactivity of the compound of the present disclosure, in the form of e.g. CuDEPP and enabling a four electron transfer, was further confirmed.

In contrast to the slow lithium insertion process in conventional Li-ion batteries, the rapid redox conversion of the electrode of the present disclosure can involve four electrons per molecule for the electrochemical reaction, which can be ascribed to the facile redox reactivity of the porphyrin complexes. The stabilization of the redox species by the highly π-conjugated structure plays an important role in sustaining excellent battery performance. The diversity of the compound of the present disclosure as an electrode-active material highlights a new approach for the molecular design of bipolar redox organic electrode.

Figure 5:
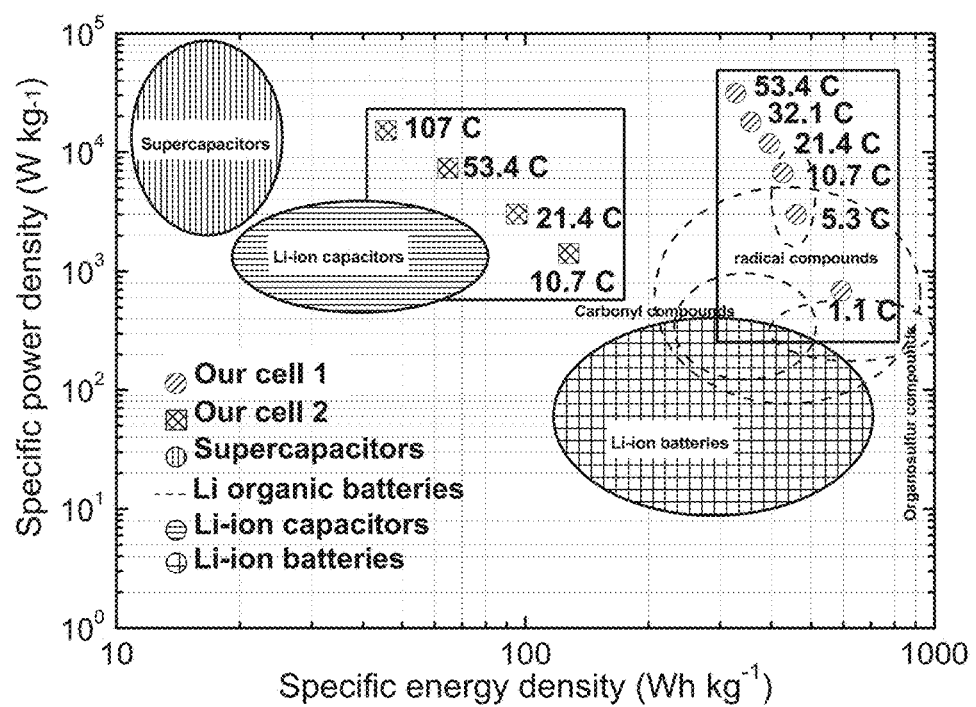
FIG. 5: Ragone plots of the energy density and power density for various energy storage systems. The battery cells indicated by circles on the top right of the plot (i.e. "Cell 1") contain CuDEPP as cathode, lithium foil as anode, and LiPF$_6$ in EC/DMC/PC solvent as the electrolyte. Four electrons can be transferred during the charge and discharge for these battery cells (i.e. between CuDEPP$^{2'}$ and CuDEPP$^{2-}$). The battery cells indicated by squares (i.e. "Cell 2") are lithium-free and contain graphite as cathode, CuDEPP as anode, and PP$_{14}$TFSI as the electrolyte. Theoretically, two electrons can be transferred during the charge and discharge of these cells (i.e. between CuDEPP and CuDEPP$^{2-}$).

In particular, the introduction of at least one alkynyl moiety, preferably ethynyl moiety, in porphyrins surprisingly resulted in compounds, which show an excellent battery performance, with storage capacities comparable to those of state-of-the art systems but with charge and discharge rates being comparable to those of capacitors and superior to those of lithium ion batteries (cf. FIG. 5). These findings can be applied to other organic compounds for electrochemical energy storage which contain alkynyl groups, and preferably ethynyl groups, as substituents that can stabilize the electrode in a formation step, leading to an electrically conductive network of less soluble electrode material.

EXPERIMENTAL PROCEDURES

Chemicals 5,15-Bis(trimethylsilanylethynyl)-10,20-diphenyl-21H, 23H-porphyrin was purchased from Frontier Scientific Inc. The LiPF$_6$ electrolyte was purchased from BASF. Ionic liquid PP$_{14}$TFSI was received from IOLITEC. [5,10,15,20-tetraphenylporphinato]copper(II) (CuTPP) and graphite material were purchased from Sigma-Aldrich. The graphite was dried at 473 K for 12 h under vacuum. The electrolyte containing 1 M lithium hexafluorophosphate (LiPF$_6$) in ethylene carbonate (EC):dimethyl carbonate (DMC):propylene carbonate (PC) (1:3:1 by volume) was used for testing the electrochemical performance of Li/LiPF$_6$/CuDEPP and CuDEPP/LiPF$_6$/CuDEPP cells. The ionic liquid of 1-butyl-1-methylpiperidinium bis(trifluoromethylsulfonyl)imide (PP$_{14}$TFSI, 99%, IoLiTech) dried at 358 K for 72 h under vacuum was used as an electrolyte for the CuDEPP/PP$_{14}$TFSI/graphite cell. All other chemicals were purchased from Sigma Aldrich. THF was distilled from sodium prior to use. Et$_3$N was distilled over CaH$_2$ and stored under argon. PP$_{14}$TFSI was dried at 80° C. in vacuum for 24 hours.

Materials Characterization

Thin-layer chromatography was performed on aluminum plates pre-coated with Merck 5735 silica gel 60 F$_{254}$. Column chromatography was performed with Merck silica gel 60 (230-400 mesh). $^1$H NMR and $^{13}$C NMR spectra were recorded on a Bruker DRX 500 spectrometer; chemical shifts are given in ppm, referenced to residual proton resonances of the solvents. UV-vis spectra were measured on a Varian Cary 500 Scan UV/vis/NIR spectrophotometer. The matrix-assisted laser desorption ionization time-of-flight (MALDI-ToF) mass spectroscopy measurements were carried out on a Synapt G2-S HDMS spectrometry workstation. IR spectra were measured in KBr pellets on MAGNA FTIR 750, Nicolet. Scanning electron microscope (SEM) measurements were carried out using a ZEISS LEO 1530 instrument. Powder X-ray diffraction (XRD) patterns were recorded in transmission geometry using a STOE STADI-P diffractometer (operated at 40 kV, 40 mA). The thermogravimetric analysis (TGA) was conducted by a SETARAM SENSYS Evo thermal analyzer under airflow (20 mL min$^{-1}$) with a heating rate of 5° C. min$^{-1}$.

Electrochemical Measurements

Electrochemical measurements were performed using a 2032 coin-type cell. A Whatman glass fiber sheet was used as separator. The assembly of the cells was conducted in an argon filled MBRAUN glove box with water and oxygen concentrations below 0.1 ppm. The cells were placed in an incubator to maintain a constant temperature of 25±0.1° C. Galvanostatic charge-discharge measurements were performed using an Arbin battery tester. Cyclic voltammetry (CV) measurements were conducted using a Biologic VMP-3 potentiostat. For galvanostatic charge-discharge measurements, the charge-discharge voltage range of cell 1 (Example 3) was between 4.5 V and 1.8 V. The open circuit voltage of the cell 1 was 3.0±0.1 V and it was firstly charged to 4.5 V. The charge-discharge voltage range of cell 2 (Example 6) was between 4.0 V and 0.0 V. The open circuit voltage of the cell 2 was 0±0.1 V and it was firstly charged to 4.0 V. The charge-discharge voltage range of cell 3 (Example 7) were between 2.8 V and 0.0 V or between 2.6 V and (−1.8) V. The open circuit voltage of the cell 3 was 0±0.1 V. The current density, 1 C=187 mA g$^{-1}$ is for four electrons transfer and 1 C=93 mA g$^{-1}$ is for two electrons transfer.

Example 1: Synthesis of CuDEPP

Figure 6:
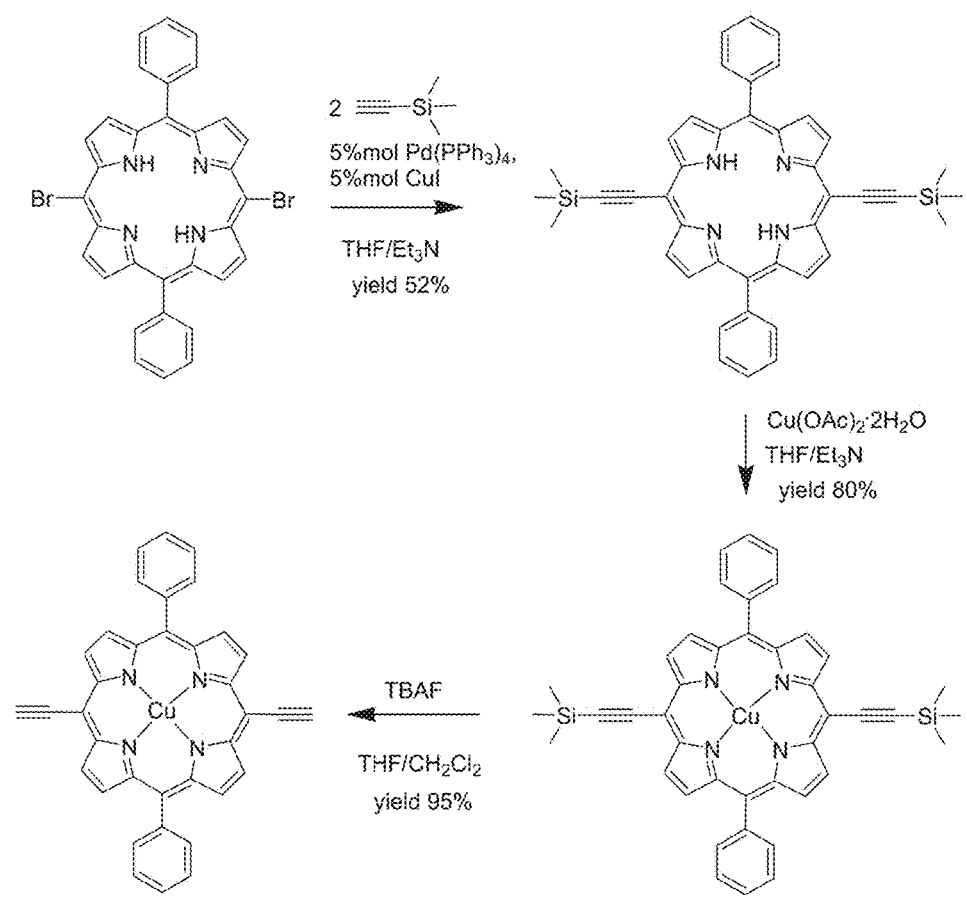
FIG. 6: Synthesis of CuDEPP starting from 5,15-dibromo-10,20-diphenyl-21H,23H-porphyrin.

CuDEPP was synthesized as depicted in FIG. 6. Reactions requiring an inert gas atmosphere were conducted under argon, and the glassware was oven-dried (140° C.).

5,15-Bis(trimethylsilanylethynyl)-10,20-diphenyl-21H,23H-porphyrin 5,15-dibromo-10,20-diphenyl-21H,23H-porphyrin (0.620 g, 1 mmol), Pd(PPh$_3$)$_2$Cl$_2$ (0.070 g, 0.1 mmol), CuI (0.040 g, 0.2 mmol) and ethynyltrimethylsilane (0.206 g, 2.2 mmol) were added into a mixture of THF (35 mL) and triethylamine (15 mL) under an argon atmosphere. The reaction mixture was stirred at room temperature for 12 hours. Then the solution was poured into 150 mL water and extracted by CH$_2$Cl$_2$ (3*50 mL). Solvents were removed in vacuum and the residue was purified by column chromatography on silica gel (hexane: CH$_2$Cl$_2$=1:1) affording brown purple solid of 5,15-Bis(trimethylsilanylethynyl)-10,20-diphenyl-21H,23H-porphyrin (0.344 g, yield 52%).

$^1$H NMR (500 MHz, CDCl$_3$) δ ppm 9.63 (d, J=4.68 Hz, 4H, pyrrole-H), 8.85 (d, J=4.65 Hz, 4H, pyrrole-H), 8.20 (d, J=6.14 Hz, 4H, Ph-H), 7.94-7.73 (m, 6H, Ph-H), 0.63 (s, 18H, —Si(CH$_3$)$_3$), −2.16 (s, 2H, pyrrole —NH). $^{13}$C NMR (126 MHz, CDCl$_3$) δ ppm 141.35, 134.55, 128.01, 126.94, 121.81, 106.87, 102.75, 100.88, 0.336. UV-vis (CH$_2$Cl$_2$, nm) 434, 508, 541, 582, 678. NIR (KBr cm$^{-1}$) 3428, 3319, 2956, 2924 (Si(C—H$_3$)$_3$), 2853, 2141 (C≡C), 1597, 1558, 1441, 1467, 1441, 1398, 1337, 1247, 1194, 1138, 1069, 1002, 974, 964, 844, 797, 704, 657, 418. ESI ToF Calc. for C$_{42}$H$_{39}$N$_4$Si$_2$: [MH$^+$], 655.3; Found: m/z 655.2.

[5,15-Bis(trimethylsilylethynyl)-10,20-diphenyl)porphinato]copper(II)

Cu(OAc)$_2$.H$_2$O (0.400 g, 2 mmol) was added to a solution of 5,15-bis(trimethylsilanylethynyl)-10,20-diphenyl-21H,23H-porphyrin (0.332 g, 0.6 mmol) in a mixture of 50 mL THF, 50 mL CH$_2$Cl$_2$ and 5 mL Et$_3$N. The reaction was stirred at room temperature for 12 hours, then poured into 150 mL water and extracted by CH$_2$Cl$_2$ (3*50 mL). The CH$_2$Cl$_2$ solution was concentrated under reduced pressure and yields a dark purple solid (0.343 g, 80%).

UV-vis (CH$_2$Cl$_2$, nm) 432, 564, 606. NIR (KBr cm$^{-1}$) 2917 (Si(C—H$_3$)$_3$), 2849, 2134 (C≡C), 1523, 1462, 1443, 1344, 1246, 1209, 1166, 1067, 1004, 993, 840, 794, 755, 706, 666, 620, 566. ESI ToF Calc. for C$_{42}$H$_{36}$N$_4$Si$_2$: [M$^+$], 715.2; Found: m/z 715.2.

[5,15-Bis(ethynyl)-10,20-diphenylporphinato]copper(II)

[5,15-Bis(trimethylsilylethynyl)-10,20-diphenyl)porphinato]copper(II) (0.322 g, 0.45 mmol) was dissolved in THF (50 mL) under an argon atmosphere at 0° C. Then tetrabutylammonium fluoride (0.252 g, 0.8 mmol) was added. After 30 min, the reaction was poured into 50 mL MeOH. The precipitate was filtered and washed by 100 mL MeOH. The product was collected to yield [5,15-Bis(ethynyl)-10,20-diphenylporphinato]copper(II) as a dark purple solid (0.244 g, 95%).

UV-vis (CH$_2$Cl$_2$, nm) 425, 558, 598. NIR (KBr cm$^{-1}$) 3264 (CC—H), 2096 ((C≡C), 1596, 1521, 1443, 1347, 1211, 1174, 1070, 1004, 936, 796, 751, 737, 711, 701, 676, 666, 646, 614, 503. MALDI ToF calc. for C$_{36}$H$_{20}$N$_4$Cu: [M$^-$], 571.1; Found: m/z 571.0.

Example 2: Formation of a CuDEPP Electrode Comprising CuDEPP, a Binder and an Electrically Conductive Additive For preparing a CuDEPP electrode first a slurry was prepared by mixing CuDEPP (50 wt %) with carbon black (40 wt %) and a polyvinylidene fluoride binder (PVDF, 10 wt %) in N-methylpyrrolidone (NMP) as solvent. The obtained slurry was then coated on a stainless steel current collector and dried at 373 K for 10 h. The mass loading of the electrode was approximately 1.0 mg cm$^{-2}$.

Example 3: Battery System Comprising a CuDEPP Cathode

A battery system (i.e. Li/LiPF$_6$/CuDEPP) was constructed according to the redox mechanism as illustrated in FIG. 2 by using lithium foil as anode, the CuDEPP electrode of Example 2 as a cathode, and an electrolyte solution of 1 M LiPF$_6$ in a solvent mixture (EC:PC:DMC=1:1:3 by volume ratio) of ethylene carbonate (EC), dimethyl carbonate (DMC), and propylene carbonate (PC).

Determination of the Working Potential Window of the Cell of Example 3

Figure 7:
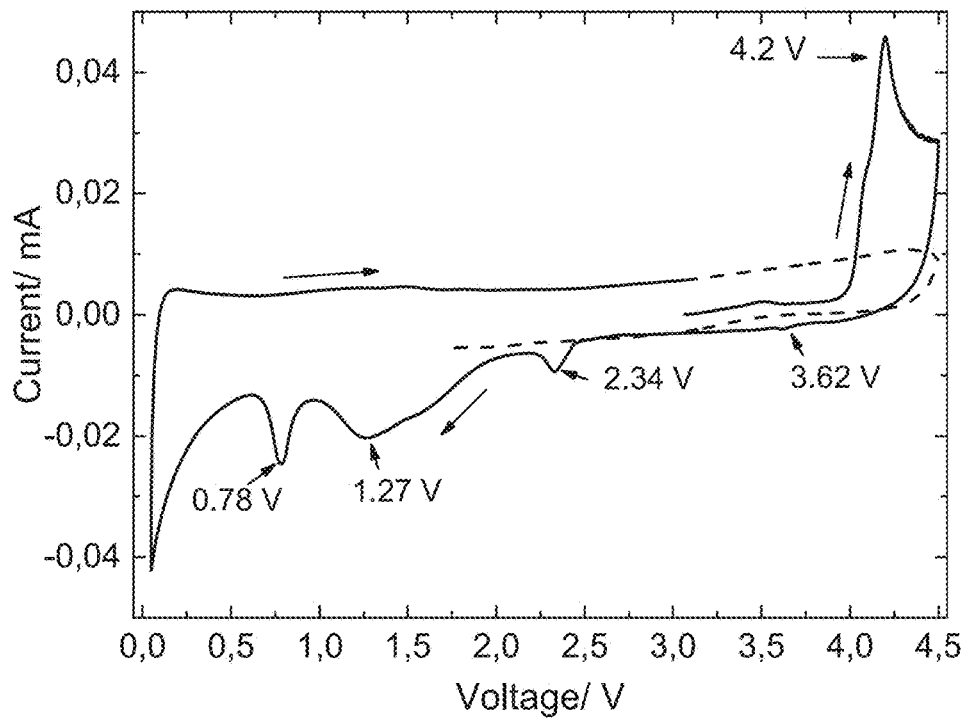
FIGS. 7 and 8: Cyclic voltammogramm (CV) investigation of a Li/LiPF$_6$/CuDEPP cell. The CV curve of the Li/LiPF$_6$/CuDEPP cell in the first cycle in a voltage range of 4.5-0.05 V (FIG. 7) and CV curves of initial five cycles in a voltage range of 4.5-1.8 V (FIG. 8). The scan rate was 0.1 mV s$^{-1}$.
Figure 8:
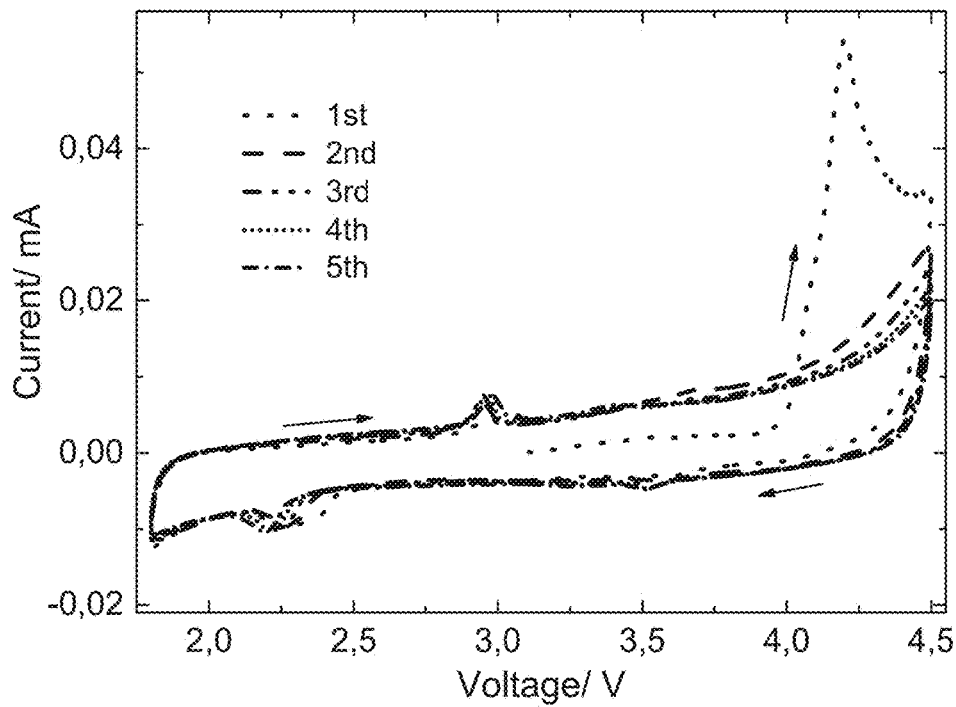

To determine the corresponding working potential window of the cell of Example 3, the cyclic voltammograms with a two-electrode cell system using the CuDEPP electrode of Example 2 as working electrode and a Li foil as the counter electrode in a voltage range of 4.5-0.05 V and 4.5-1.8 V (vs Li/Li*), respectively, was recorded. The strong oxidative peak shown in FIG. 7 at 4.2 V can be assigned to the oxidation of CuDEPP to [CuDEPP]$^{2+}$ and a possible polymerization of the ethynyl units. The cathodic peak at 2.34 V corresponds to the reductions at the porphyrin core e.g. CuDEPP$^{2+}$ to CuDEPP$^{2-}$. The lowest irreversible reductive signals at about 1.27 and 0.78 V are probably associated with the reduction of the center Cu(II) to Cu(I) and/or other side reactions. In the voltage range of 4.5 to 1.8 V (as shown in FIG. 8), the reversible redox pair at 2.24 and 2.90 V relates to the redox reaction of the CuDEPP. The weak intensity of the redox peaks may be caused by the faster electron transfer process among the CuDEPP species, which is also reflected in the sloping discharge/charge profiles described herein below.

Figure 9:
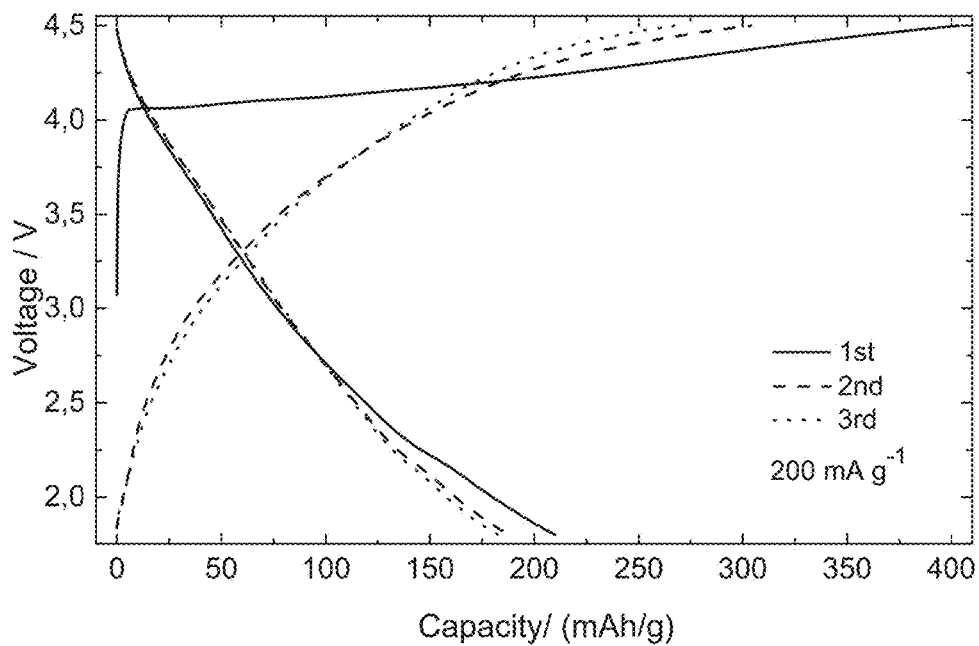
FIGS. 9 to 13: Electrochemical performance of a CuDEPP cathode in a voltage range of 4.5-1.8 V: initial charge and discharge curves (FIG. 9); dQ/dV plot of the discharge curve in FIG. 9 (FIG. 10); charge and discharge performance at different current rates (FIG. 11); discharge curves at different current rates (FIG. 12); and the selected charge/discharge profiles at a high current density of 10 A g$^{-1}$ (FIG. 13).
Figure 10:
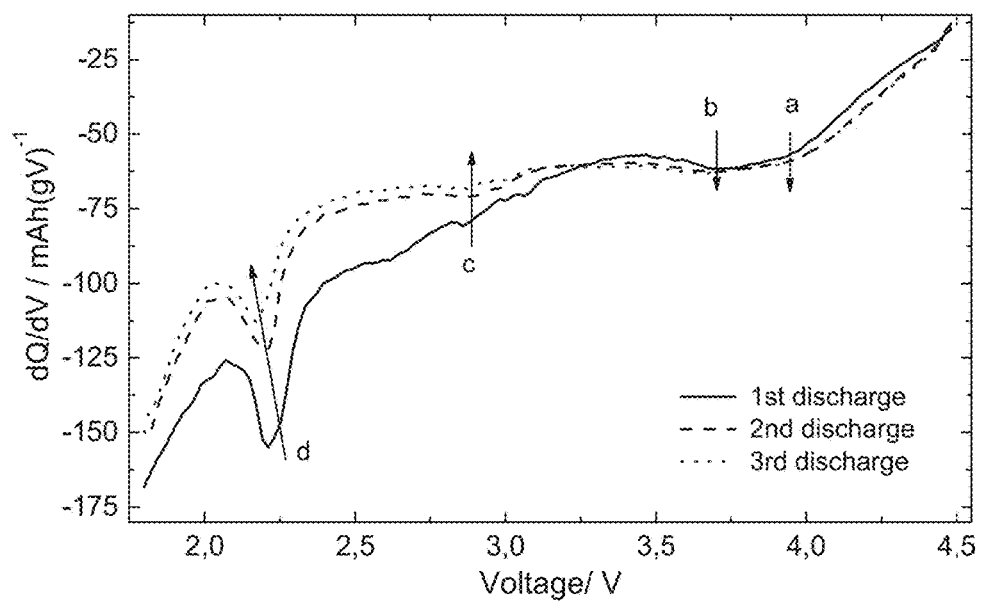

Examination of the Electrochemical Performance of CuDEPP as a Cathode in the Galvanostatic Charge/Discharge Tests The voltage range of 4.5-1.8 V was accordingly applied to examine the electrochemical performance of the CuDEPP as a cathode in the galvanostatic charge/discharge tests. The first charge capacity was approximately 400 mAh g$^{-1}$ at a current density of 200 mA g$^{-1}$ (FIG. 9), which is higher than the value estimated by two-electron oxidation from the CuDEPP to CuDEPP$^{2+}$ (The specific capacity was calculated based on the mass of CuDEPP, theoretical capacity of the CuDEPP electrode is 47 mAh g$^{-1}$ for one-electron transfer). Considering the flat voltage plateau and the corresponding intense CV signal at about 4.2 V during the first anodic sweeping, the surface side reaction of porphyrin molecule with liquid electrolyte and/or the polymerization of the initial CuDEPP might take place during the first charge process. The vanishing of the characteristic vibration bands at 3264 cm$^{-1}$ for —C≡C—H and at 2096 cm$^{-1}$ for —C≡C—, observed in the ex-situ IR spectra of the CuDEPP electrode after the first cycle, implies the same. The first discharge capacity was about 210 mAh g$^{-1}$ and gradually decreased to 182 mAh g$^{-1}$ in the third cycle which is close to the theoretical value of 187 mAh g$^{-1}$ based on the four-electron reaction from the dication to the dianionic species of the molecule (CuDEPP$^{2+}$→CuDEPP$^{2-}$, vice versa for the recharge process). Interestingly, a highly reversible discharge and charge profile was observed upon cycling after the first charge, delivering an average output voltage of about 3 V. No well-defined voltage plateaus were observed in charge/discharge profiles of the Li/LiPF$_6$/CuDEPP cell, implying a fast electron transfer process through a solid solution reaction mechanism rather than a two-phase transition mechanism. In addition, the subtle discharge behaviors were indicated in a dQ/dV plot of initial cycles as shown in FIG. 10, in which four potential peaks at 3.94, 3.69, 2.88 and 2.2 V were revealed.

Evaluation of the Cycling and Rate Performance

Figure 11:
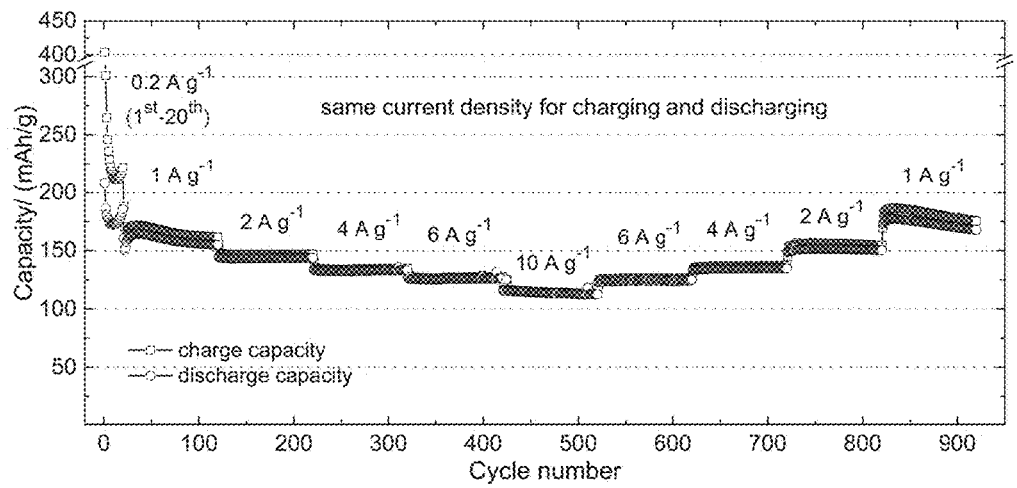
Figure 12:
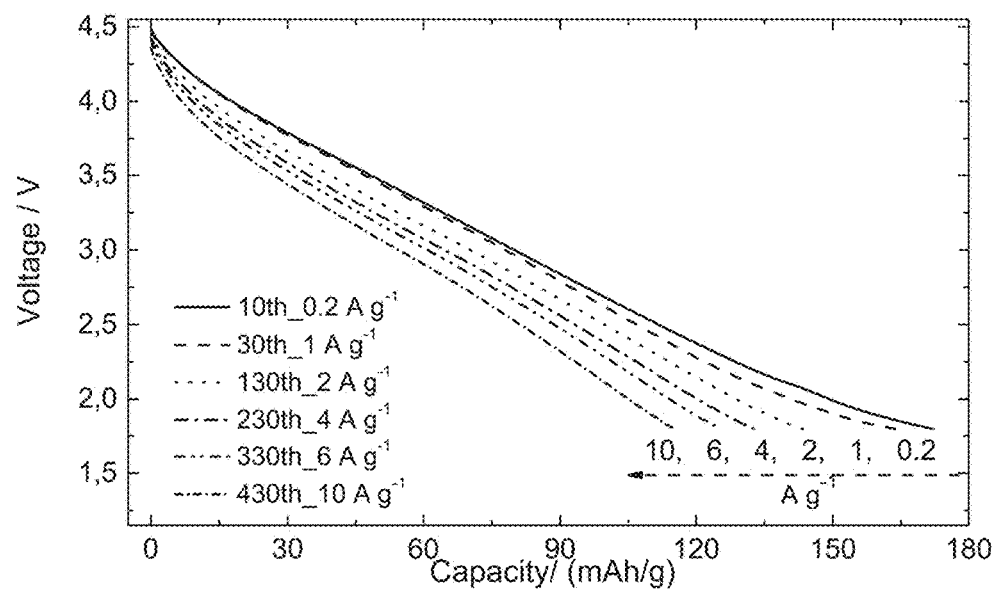
Figure 13:
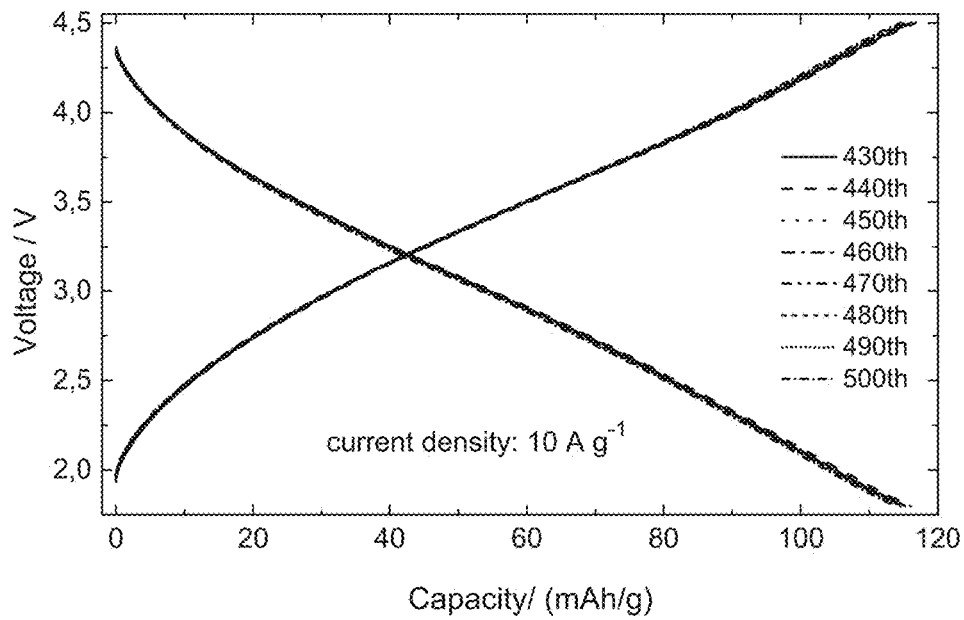

The cycling and rate performance of the cell of Example 3 was further evaluated. As shown in FIG. 11, the cell maintained a discharge capacity of about 185 mAh g$^{-1}$ with a coulombic efficiency of 84% after the initial 20 cycles at a current density of 200 mA g$^{-1}$. Subsequently, the cell was cycled by applying increased current rates. The stable discharge capacities of 163, 143, 132, 125 mAh g$^{-1}$ were respectively retained at the current of from 1, 2, 4, 6 and 10 A g$^{-1}$ within a period of about 100 cycles. Moreover, the discharge capacities of the CuDEPP electrode were mostly retrieved by stepwise tuning the current from 10 to 1 A g$^{-1}$. The selected discharge curves of the CuDEPP electrode at different current rates are shown in FIG. 12, which presents slightly decreased potentials upon increasing the discharge rate. Remarkably, even at a high current density of 10 A g$^{-1}$, the CuDEPP electrode could still deliver a stable reversible discharge capacity of 115 mAh g$^{-1}$, which was obtained within 42 seconds with a coulombic efficiency of 99.5%, demonstrating an excellent electrochemical performance. This value corresponds to a specific energy density of 345 Wh kg$^{-1}$ and a specific power of 29.5 KW Kg$^{-1}$, which is competitive with some of supercapacitors. The outstanding cyclability at the extremely high current density of 10 A g$^{-1}$ was represented in the characteristic charge/discharge profiles (FIG. 13).

Figure 14:
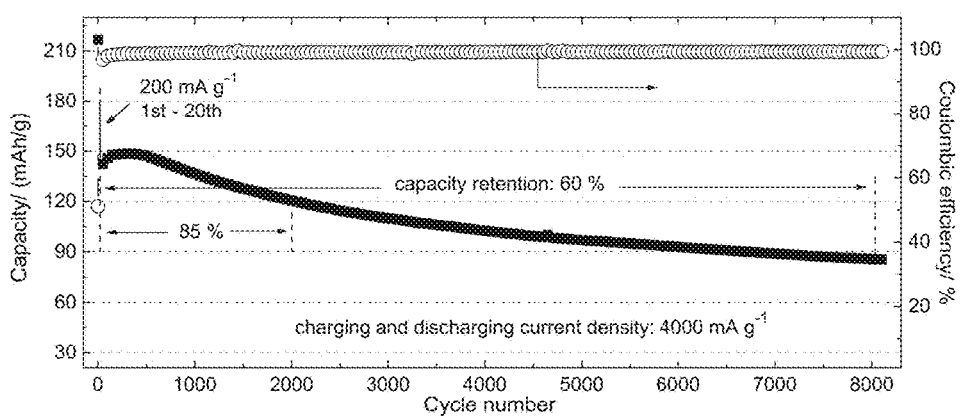
FIGS. 14 to 18: Long-term cycling of a Li/LiPF$_6$/CuDEPP cell: cycling performance (FIG. 14); selected charge and discharge curves at a current of 4 A g$^{-1}$ (FIGS. 15 and 16); CV curves of the Li/LiPF$_6$/CuDEPP cell after 2000 cycles in a battery test at a sweeping rate of 10 mV s$^{-1}$ (FIG. 17) and 100 mV s$^{-1}$ (FIG. 18), respectively.
Figure 15:
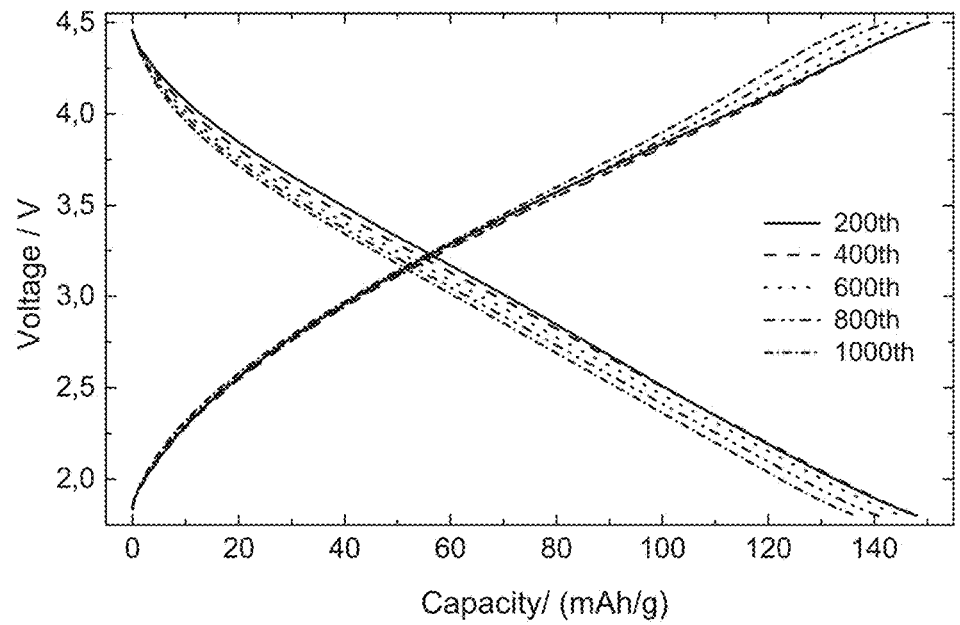
Figure 16:
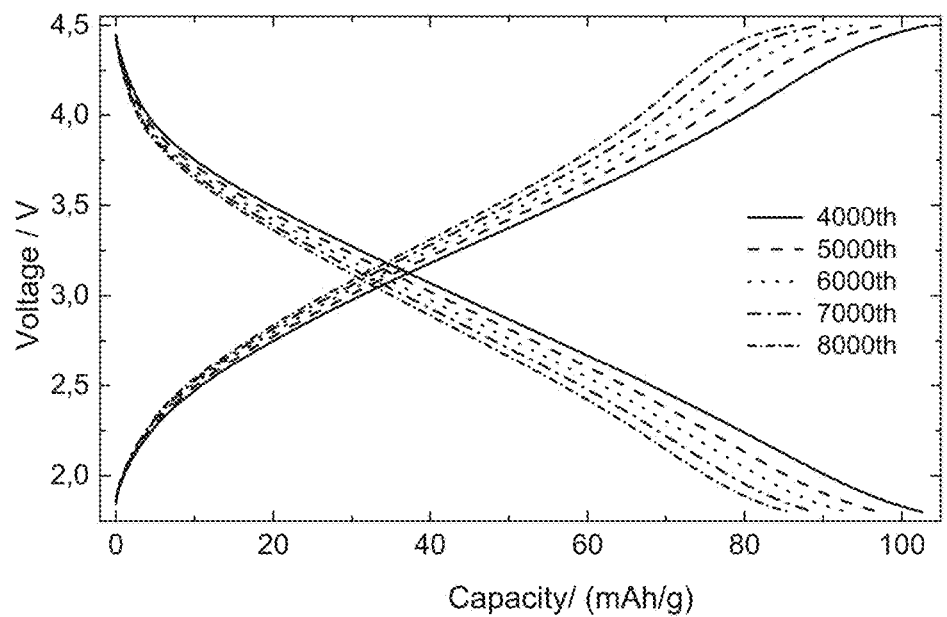
Figure 17:
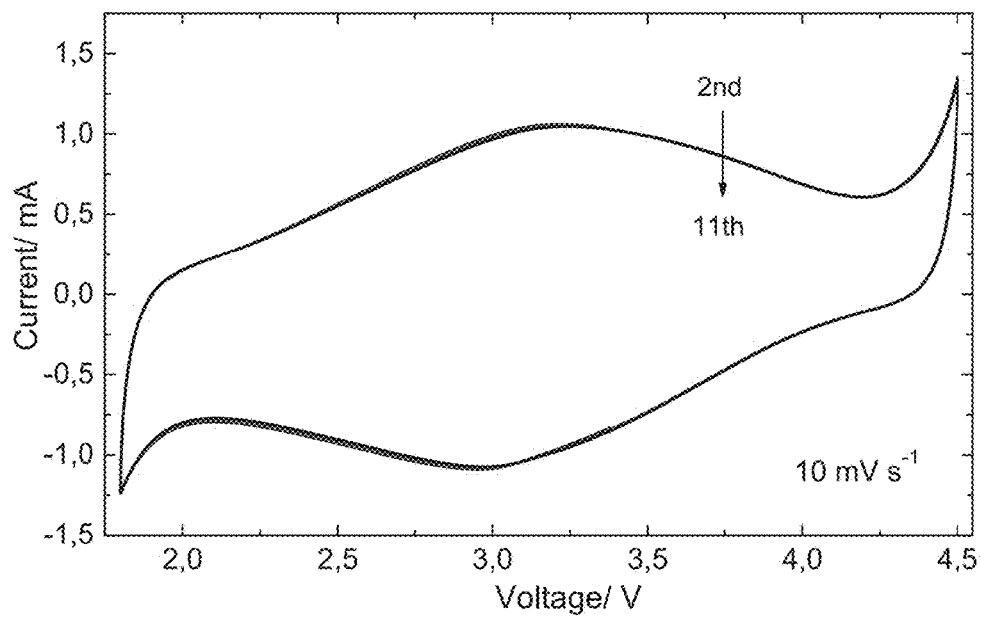
Figure 18:
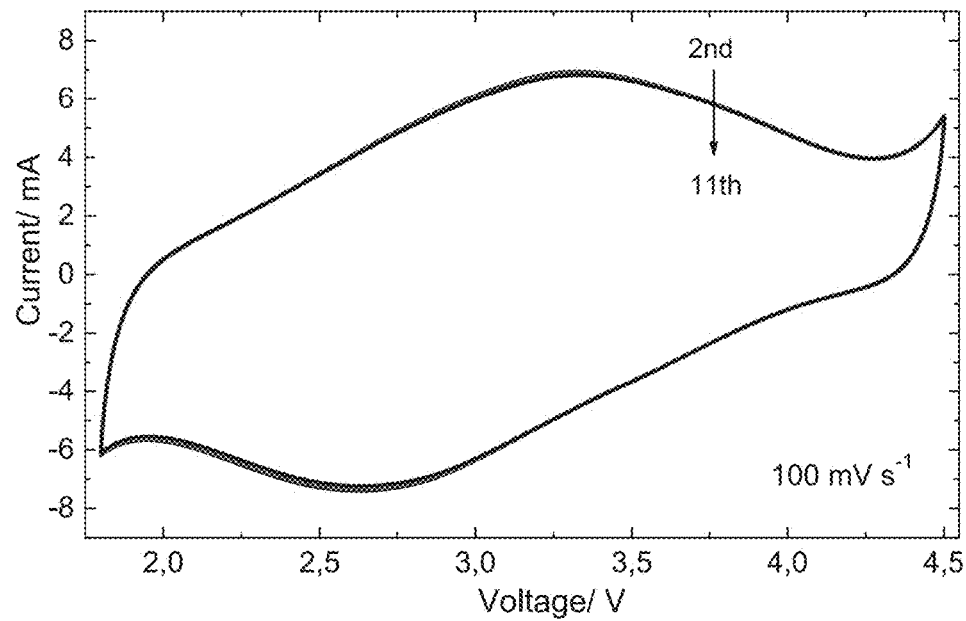

Furthermore, the long-term cycling performance of a Li/LiPF$_6$/CuDEPP cell comprising a cathode consisting of CuDEPP only at a high current density of 4 A g$^{-1}$ was also investigated. As shown in FIG. 14, the cell was initially cycled at a current density of 200 mA g$^{-1}$ for 20 cycles to "activate" the CuDEPP cathode. Subsequently, the cell was cycled at a current of 4 A g$^{-1}$ for 8100 cycles in total. A maximal capacity of 150 mAh g$^{-1}$ was obtained in the 226$^{th}$ cycle. Moreover, the capacity retention was approximately 85% for the first 2000 cycles and gradually decreased to 60% after 8000 cycles with a high coulombic efficiency (close to 100%). The selected charge and discharge profiles of the CuDEPP cathode are shown in FIGS. 15 and 16. Additional cyclic voltammograms were captured after cycling the Li/LiPF$_6$/CuDEPP cell for 2000 cycles. As shown in FIG. 17, a reversible pair of well-defined redox peaks at approximately 3 V was observed at a sweeping rate of 10 mV s$^{-1}$, which is consistent with the average discharge/charge potential of 3 V. FIG. 18 shows the high reversibility of the CV curve at a high scan rate of 100 mV s$^{-1}$, which demonstrates the excellent rate capability of the CuDEPP cathode.

Electrochemical Behavior of the Cell of Example 3, when Starting the Discharging Based in the Reaction CuDEPP+2e$^-$→CuDEPP$^{2-}$ The electrochemical behavior of the Li/LiPF$_6$/CuDEPP cell of Example 3 was also examined by starting with discharging based on the reaction CuDEPP+2e→Cu-DEPP$^{2-}$. Although the first charge curve was similar to the cell 1 described above, the discharge voltage decreased steeply from the open circuit voltage (OCV) of 3.1 V to 1.5 V, resulting in a lower reversible capacity in the subsequent cycles at a current rate of 200 mA g$^{-1}$.

Example 4: Analysis of the Morphology and Crystallinity of a CuDEPP Electrode

The morphology and crystallinity of the CuDEPP electrode material in the first cycles was analyzed by ex-situ SEM and XRD, respectively. In order to identify changes of the morphology during charge/discharge processes, pure CuDEPP was tested in a coin cell. For this purpose, the electrode was fabricated by directly pressing CuDEPP on the rough stainless steel current collector. The setup for the measurements is the same as described in Example 3.

Figure 19:
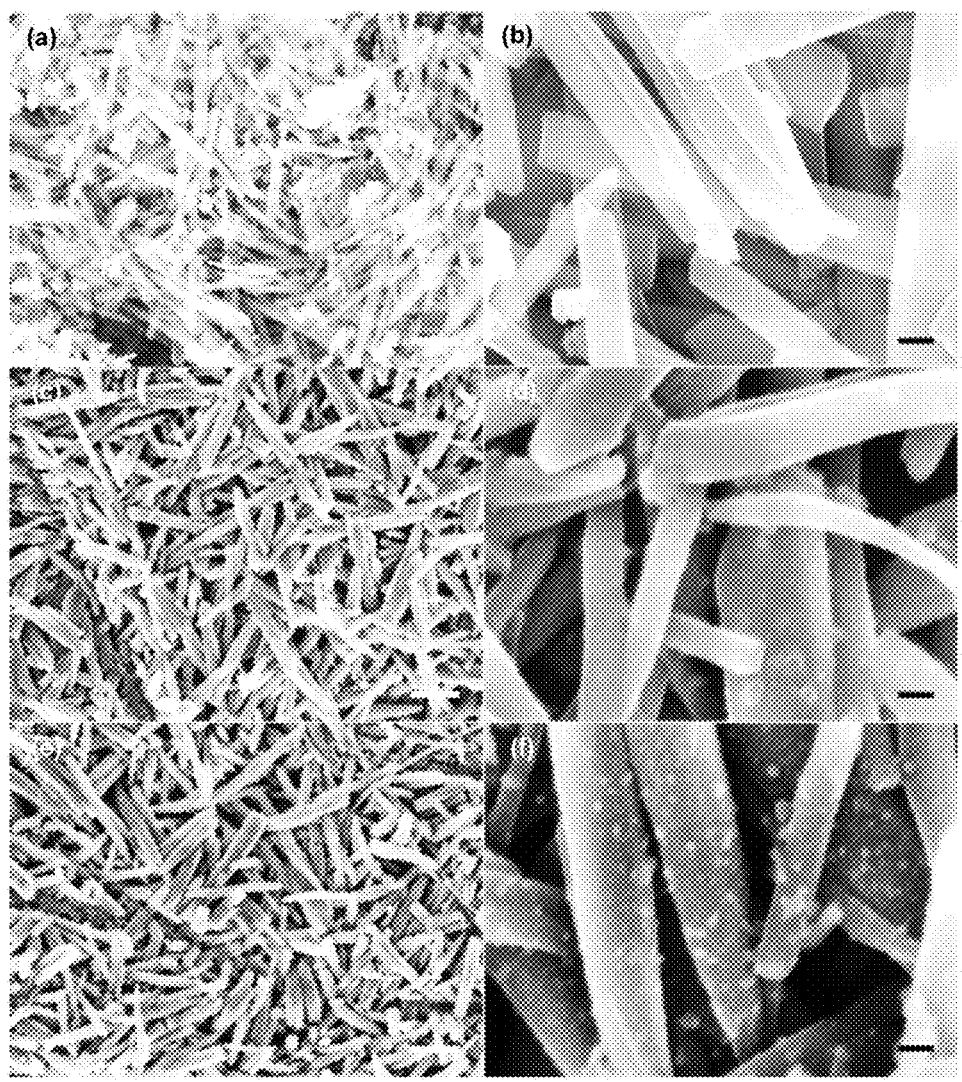
FIG. 19: Morphology and crystallinity of a CuDEPP cathode material at different electrochemical states: SEM images of the as-prepared material (FIGS. 19, *a* and *b*), the charged to 4.5 V material (FIGS. 19, *c* and *d*), and the discharged to 1.8 V material (FIGS. 19, *e* and *f*). White and black scale bars represent 2 μm and 200 nm, respectively.
Figure 20:
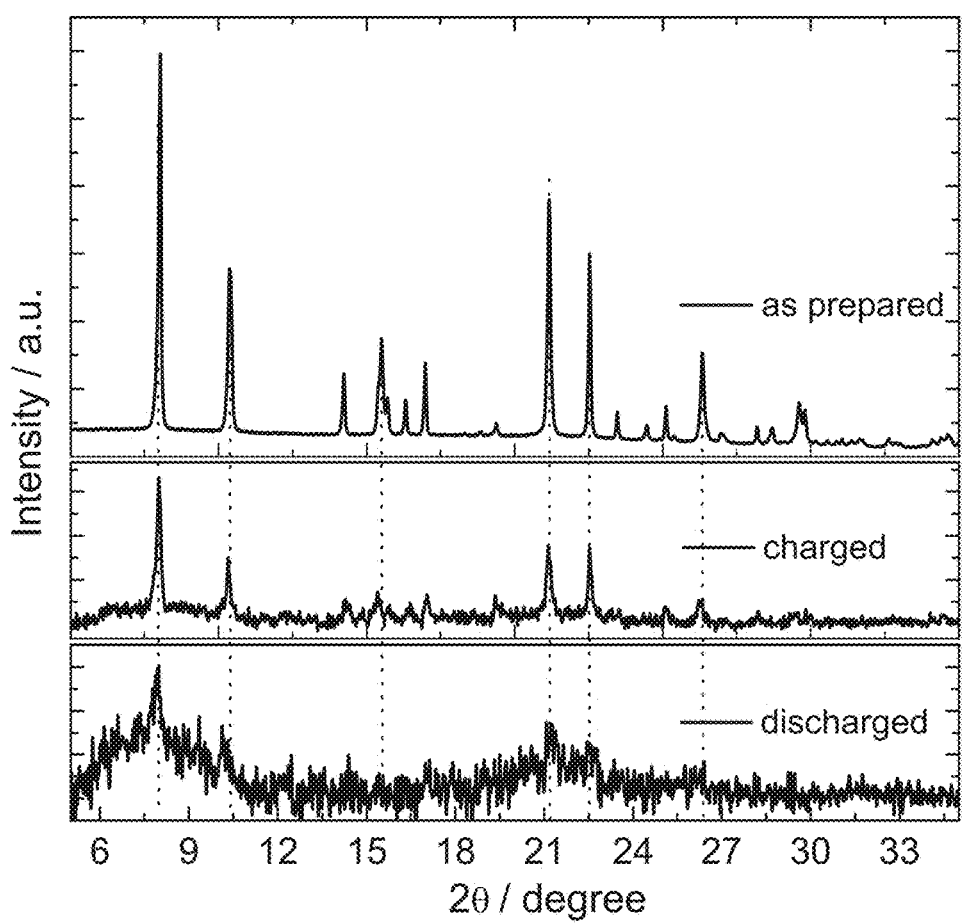
FIG. 20: Morphology and crystallinity of a CuDEPP cathode material at different electrochemical states: XRD patterns in the as-prepared scale, the charged to 4.5 V scale, and the discharged to 1.8 V scale of the CuDEPP electrode.

A stable charge and discharge capacity of 80 mAh g$^{-1}$ was obtained in the initial cycles even without the presence of conductive carbon and binder. FIGS. 19a and b show that the initial CuDEPP has a rod-like crystalline morphology with a size around 4 μm in length, 200-400 nm in width. A lowered crystallinity of the CuDEPP was observed after charge/discharge as shown in FIG. 19c-f. In accordance thereto, the sharp peaks in the XRD patterns indicate the good crystallinity of the synthesized CuDEPP material, which changed to amorphous and/or nanosized crystalline in the charged and discharged state, respectively (FIG. 20).

Example 5: Electrochemical Performance of Carbon Free CuDEPP Electrode

The CuDEPP material was directly pressed on a stainless steel and used as cathode. Using a same setup as Example 3, i.e. using lithium foil as anode and LiPF$_6$ as electrolyte, the battery performance was examined at a current density of 200 mA g$^{-1}$. An initial discharge capacity of 85 mAh g$^{-1}$ was obtained for the pure CuDEPP electrode in a voltage range of 4.5-1.8 V. In the 10$^{th}$ cycle, a discharge capacity of 80 mAh g$^{-1}$ was maintained.

Comparative Example 1: Battery System Comprising a CuTPP Electrode

The commercial available porphyrin complex [5,10,15,20-tetraphenylporphinato]copper(II) (CuTPP) was initially probed as a cathode in a battery system further comprising a Li metal anode and 1 M LiPF$_6$ in a solvent mixture (EC:PC:DMC=1:1:3 by volume ratio) of ethylene carbonate (EC), dimethyl carbonate (DMC), propylene carbonate (PC) as the electrolyte. However, the battery's performance was not satisfying, since the said cell only delivered a reversible capacity of 40 mAh g$^{-1}$ at a current density of 100 mA g$^{-1}$. This can probably be associated with the high solubility of active material in the electrolyte or other inherent limitations of its electrochemical properties.

Example 6: Battery System Comprising a CuDEPP Anode

A lithium free recharge battery (cf. FIG. 3) was formed by coupling the CuDEPP of Example 2 as an anode and graphite as an intercalation cathode in the pure ionic liquid electrolyte 1-butyl-1-methylpiperidinium bis(trifluoromethylsulfonyl)imide (PP$_{14}$TFSI).

Cyclic Voltammogram Measurements with the Battery Cell of Example 6

Figure 21:
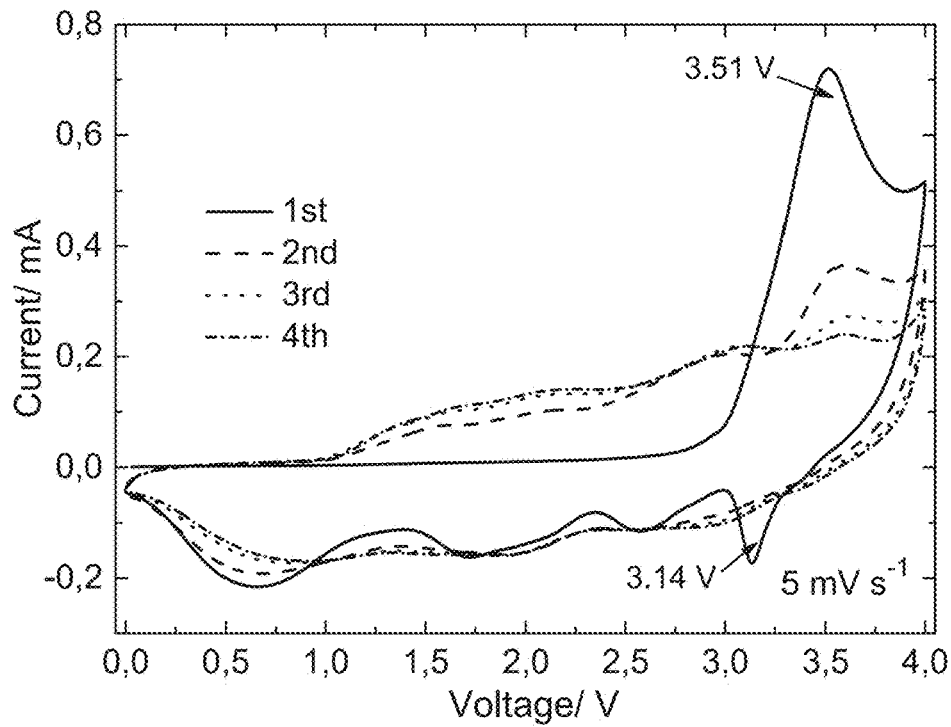
FIGS. 21 and 22: CV investigation of a CuDEPP/PP$_{14}$TFSI/graphite cell: initial CV curves of the CuDEPP/PP$_{14}$TFSI/graphite cell at a scanning rate of 5 mV s$^{-1}$ (FIG. 21) and 20 mV s$^{-1}$ (FIG. 22), with a sweeping voltage range of 4.0-0.0 V.
Figure 22:
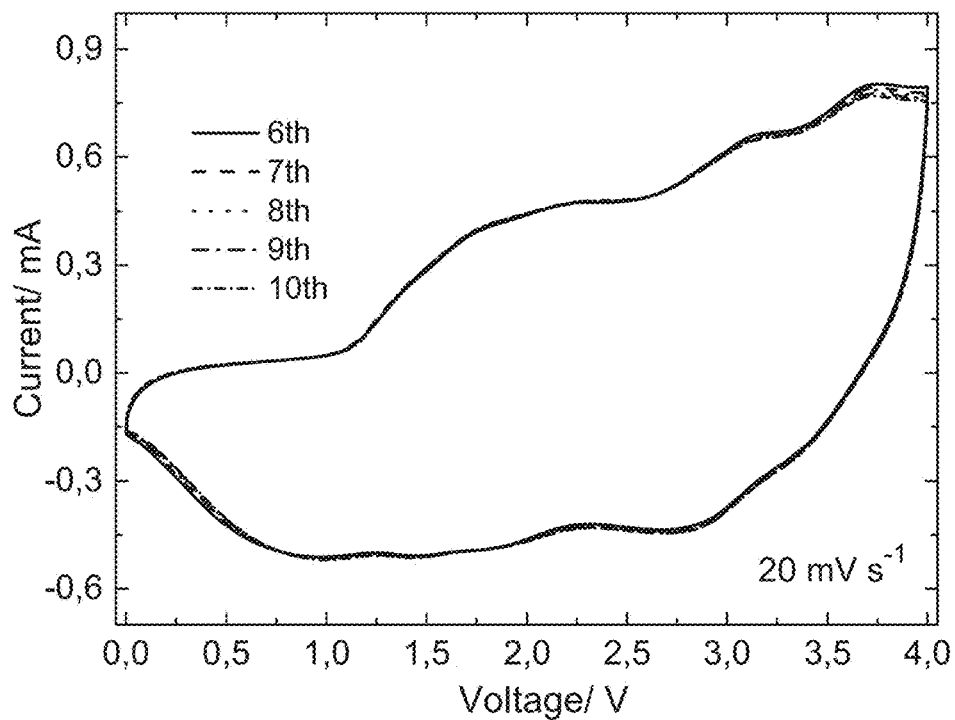
Figure 23:
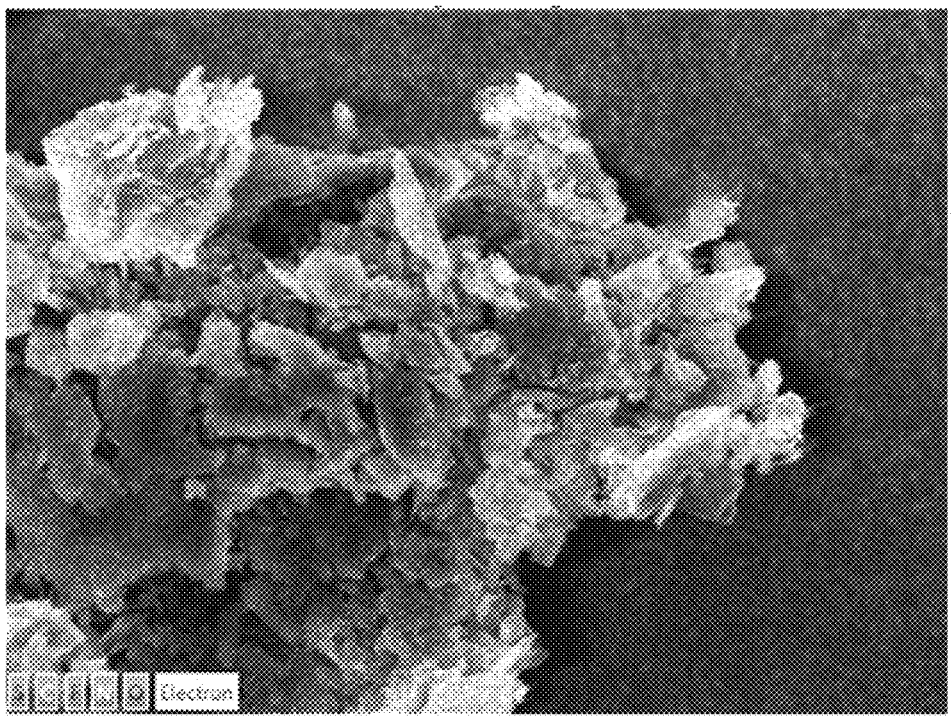
FIGS. 23 to 30: The characterizations of the graphite electrode of a CuDEPP/PP$_{14}$TFSI/graphite cell at different electrochemical states: SEM images of the charged graphite cathode (FIG. 23); the corresponding element maps denoted as carbon, oxygen, fluorine, nitrogen and sulfur, respectively (FIGS. 24 to 28); the EDX sum spectrum of the charged graphite (FIG. 29); and the XRD patterns of the graphite cathode in the as-prepared, the charged and the discharged state (FIG. 30).
Figure 24:
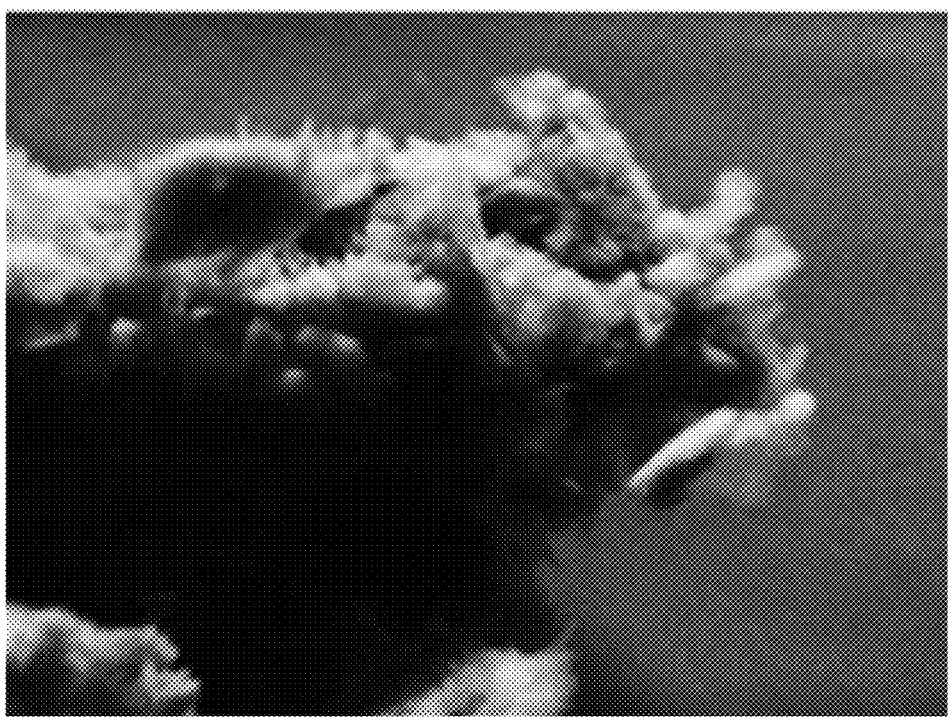
Figure 25:
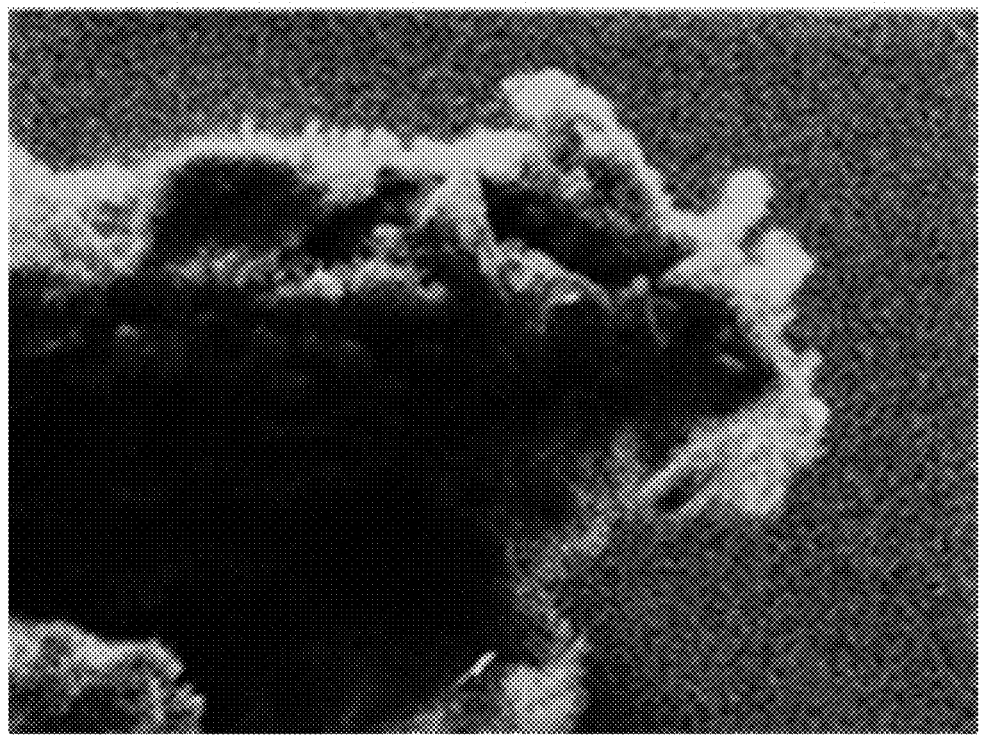
Figure 26:
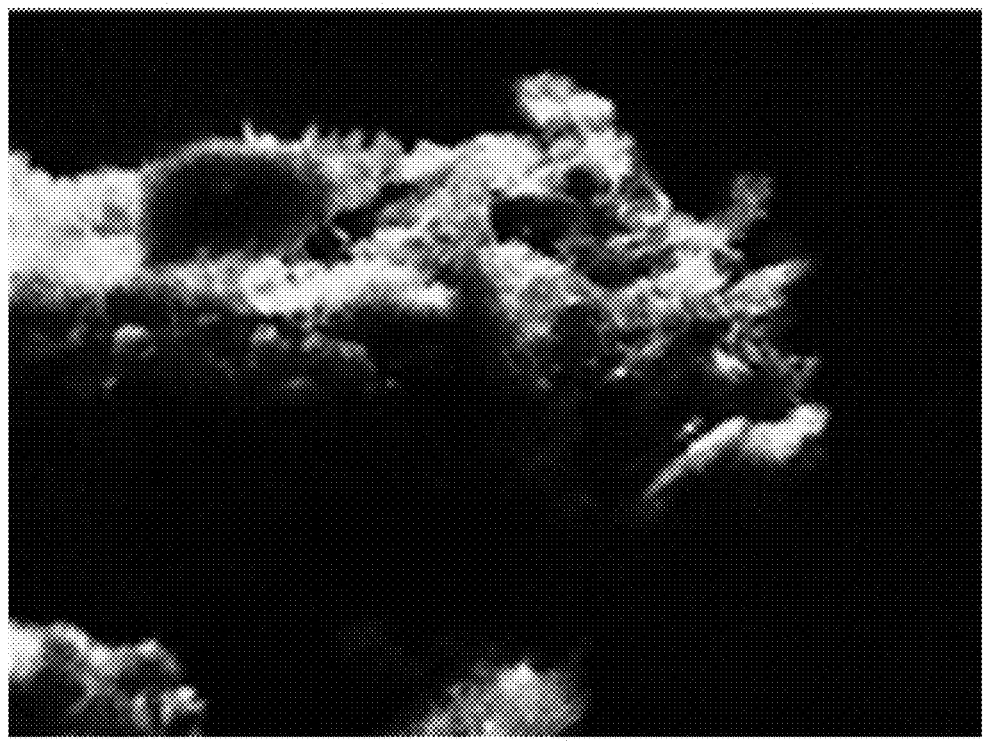
Figure 27:
Figure 28:
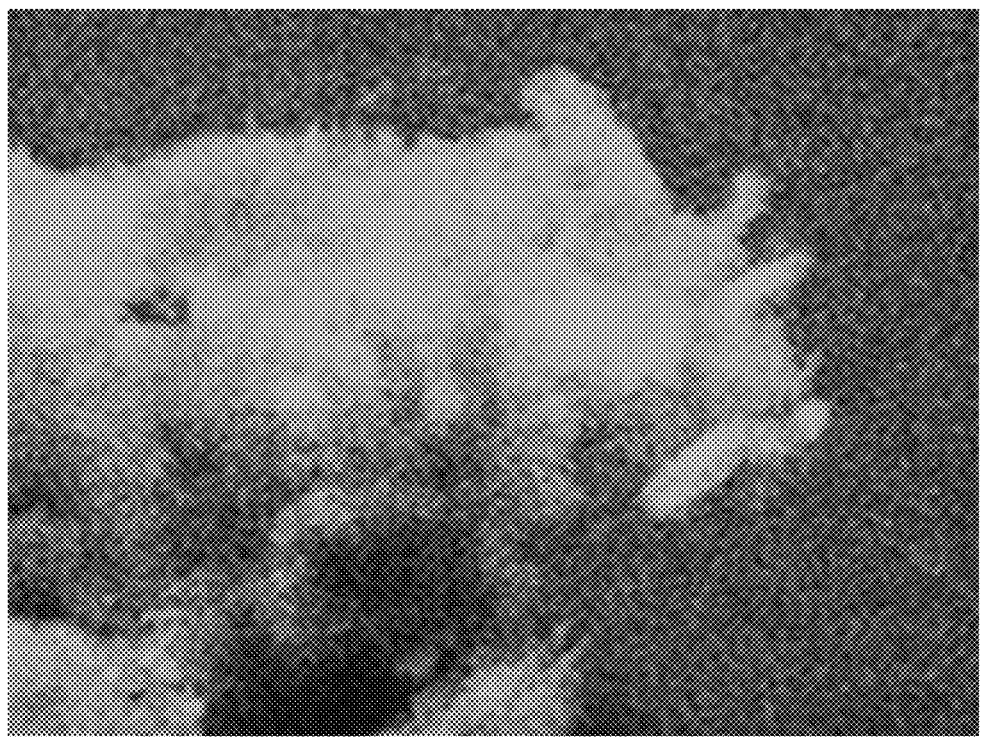

The CV measurements were performed using the graphite as working electrode and the CuDEPP electrode of Example 2 as the counter electrode in pure PP$_{14}$TFSI electrolyte in a potential range of 4.0-0.0 V at different scanning rates as shown in FIGS. 21 and 22. In the first anodic sweeping at a scan rate of 5 mV s$^{-1}$, a sharp couple of oxidation/reduction peaks were observed at 3.51/3.14 V, which are associated with the intercalation/de-intercalation of TFSI$^-$ into/from the graphite electrode. Three additional reduction peaks were observed at 2.57, 1.73 and 0.66 V in the first cathodic sweeping, indicating a multi-step electrochemical reaction related to a multi-stage de-intercalation of TFSI$^-$ anions from the graphite cathode. Moreover, a good reversibility in the subsequent scans at a scan rate of 20 mV s$^{-1}$ were observed (cf. FIG. 22), implying a good rate capability of the cell.

Verification of the Intercalation of TFSI⁻ Anions

Figure 29:
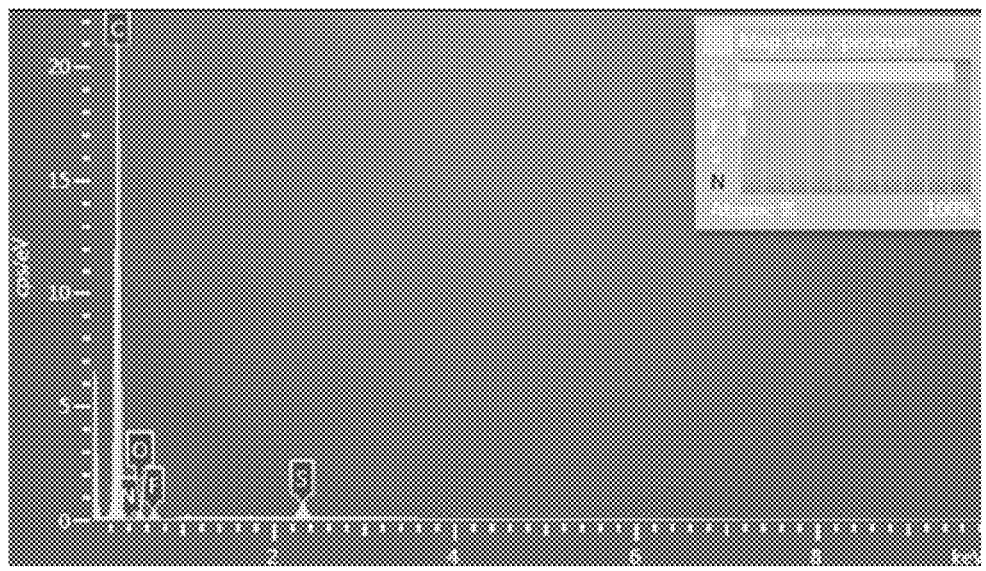
Figure 30:
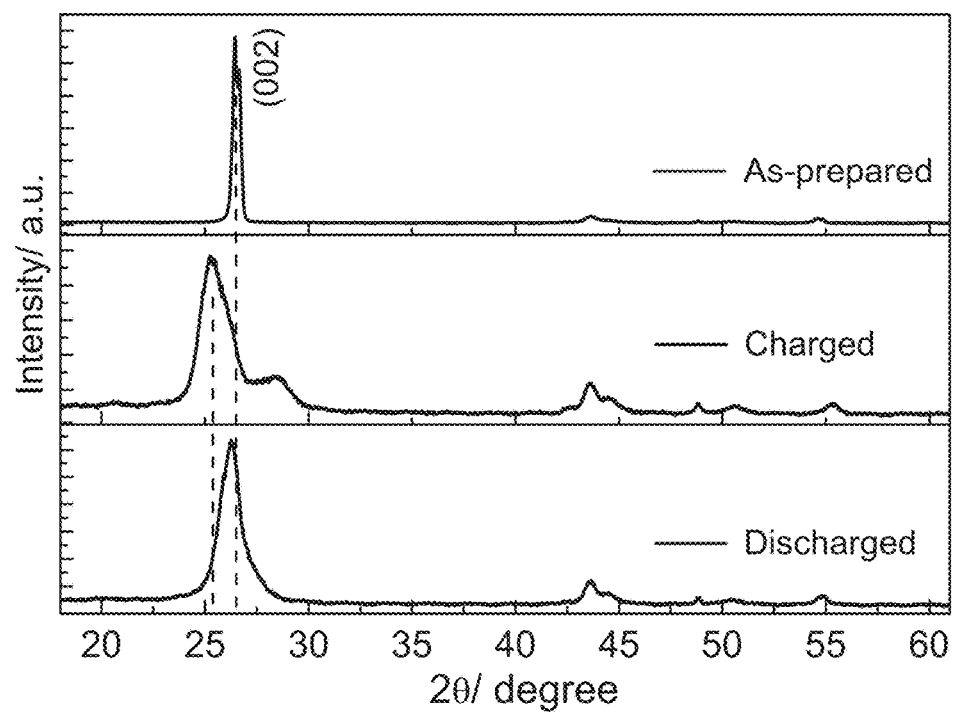

The intercalation of TFSI⁻ anions into the graphite layers was verified by means of SEM, EDX and XRD measurements. The charged/discharged graphite samples were prepared by initially charging the CuDEPP/PP$_{14}$TFSI/graphite cell of Example 6 at a current of 200 mA g$^{-1}$ to a cut-off voltage of 4 V and the subsequent discharge to 0 V. The elemental maps shown in FIGS. 23 to 28 indicated that carbon (C), oxygen (O), fluorine (F), nitrogen (N) and sulfur (S) were uniformly distributed in the charged graphite electrode. Moreover, the EDX also confirmed the presence of the TFSI⁻ species in the graphite cathode (cf. FIG. 29). Furthermore, XRD patterns in the charged graphite revealed that the characteristic 002 diffraction peak (2θ=26.4°) of graphite shifted to a low diffraction angle (2θ=25.3°), demonstrating the lattice expansion during the intercalation of the TFSI⁻ anion (cf. FIG. 30). Upon discharging, the expanded 002 diffraction peak (2θ=26.3°) was almost recovered to its original position, indicating a reversible intercalation/de-intercalation process of the TFSI⁻ anion in the graphite electrode (cf. FIG. 30).

Figure 31:
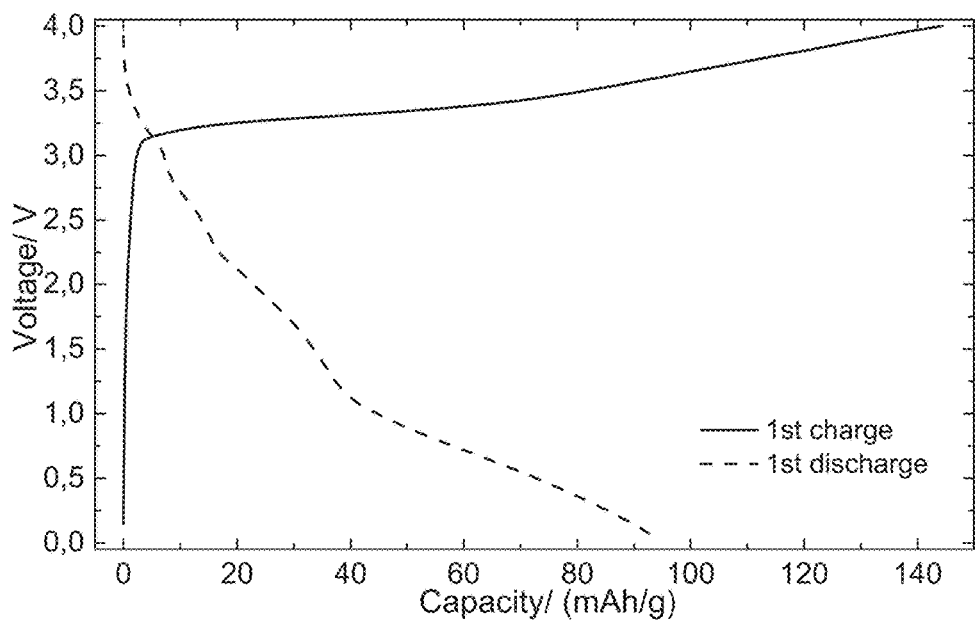
FIGS. 31 and 32: Rate performance of the CuDEPP/PP$_{14}$TFSI/graphite cell: the first charge/discharge profiles at a current density of 1 A g$^{-1}$ (FIG. 31) and the rate performances in a voltage range of 4.0-0.0 V (FIG. 32).
Figure 32:
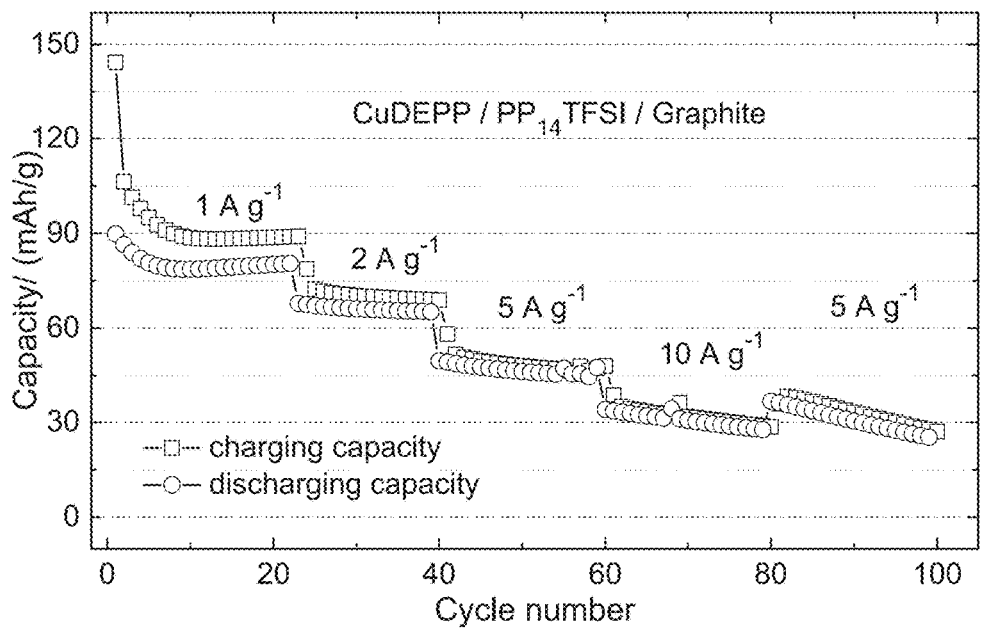
Figure 33:
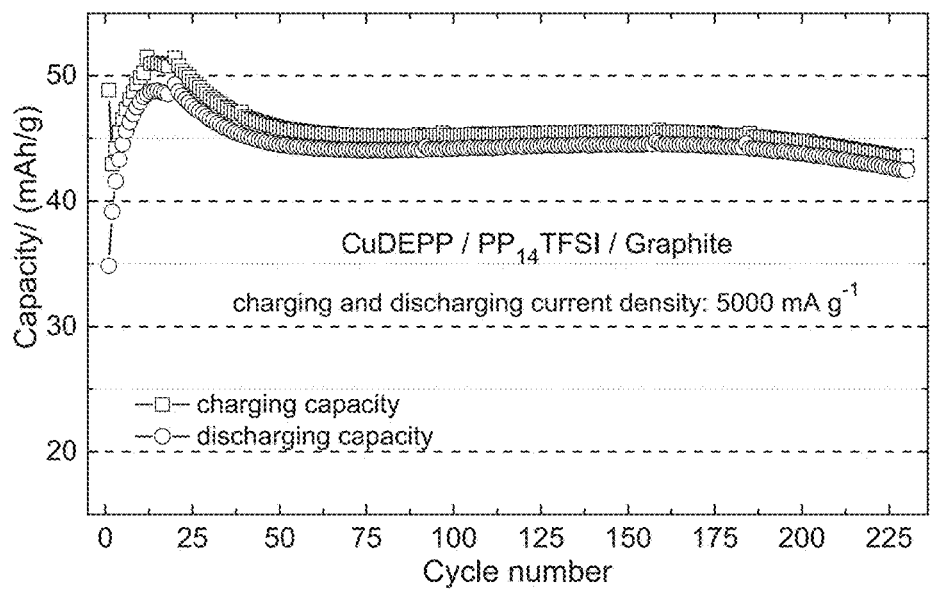
FIGS. 33 and 34: The cycling performance of the CuDEPP/PP$_{14}$TFSI/graphite cell in the voltage range of 4.0-0.0 V: cycling performance at a current density of 5 A g$^{-1}$ (FIG. 33) and selected charge/discharge curves at the 50$^{th}$, 100$^{th}$ and 150$^{th}$ cycle (FIG. 34).
Figure 34:
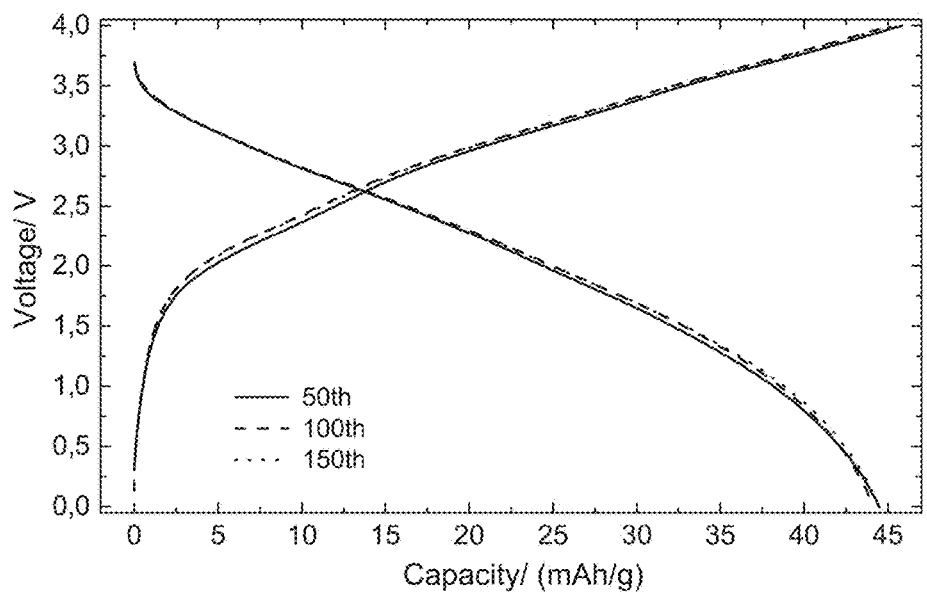

Examination of the Electrochemical Performance of CuDEPP as an Anode in the Galvanostatic Charge/Discharge Tests The galvanostatic charge-discharge tests for the CuDEPP/PP$_{14}$TFSI/graphite cell of Example 6 were carried out in a voltage range of 4.0 to 0.0 V at different current rates. The open circuit voltage (OCV) of the cell was close to 0 V (24 mV). A slopping curve is observed in the discharge profile at a current of 1 A g$^{-1}$ delivering a capacity of 94 mAh g$^{-1}$ (cf. FIG. 31), which is close to the theoretical value of the CuDEPP anode based on a two electron transfer (CuDEPP→CuDEPP$^{2-}$, 93.5 mAh g$^{-1}$). Good cycling reversibility and rate capability were also achieved at current rates from 1 to 10 A g$^{-1}$ as shown in FIG. 32. Notably, a reversible discharge capacity of 32 mAh g$^{-1}$ was obtained within 12 seconds at a current density of 10 A g$^{-1}$ using such a Li metal free rechargeable battery system, which corresponds to a high specific power of 19 kW kg$^{-1}$. The cycling performance of the CuDEPP/PP$_{14}$TFSI/graphite cell was tested at a high constant current density of 5 A g$^{-1}$ (53 C) and a stable discharge capacity of 44 mAh g$^{-1}$ was provided up to 200 cycles after the stabilization of the cell in initial cycles (cf. FIG. 32). The selected charge/discharge curves in a voltage range from 4.0 to 0.0 V are shown in FIG. 33, demonstrating a highly reversible and stable performance at a high current rate.

Example 7: All-Organic Battery System Comprising a CuDEPP Anode and a CuDEPP Cathode A symmetric cell comprising the CuDEPP electrode of Example 2 both as a cathode and an anode material as well as an electrolyte solution of 1 M LiPF$_6$ in a solvent mixture (EC:PC:DMC=1:1:3 by volume ratio) of ethylene carbonate (EC), dimethyl carbonate (DMC), and propylene carbonate (PC) was produced.

Electrochemical Properties of the Cell of Example 7

Figure 35:
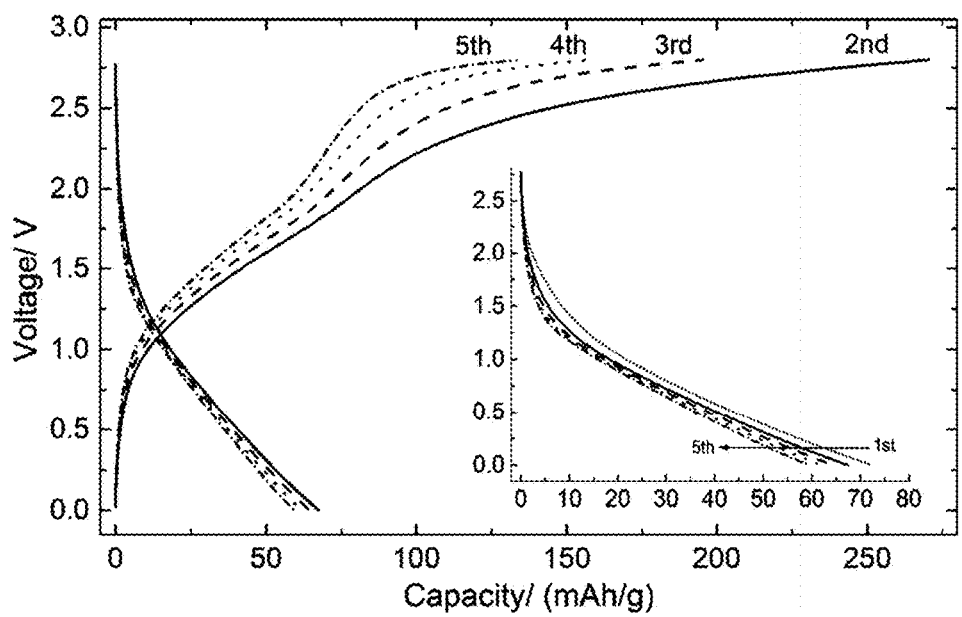
FIGS. 35 and 36: Charge/discharge profiles of a symmetric CuDEPP/LiPF$_6$/CuDEPP cell: selected charge-discharge curves in the voltage range of 2.8-0.0 V at a current density of 200 mA g$^{-1}$ (FIG. 35; insert depicts the initial discharge curves) and selected charge-discharge curves 2.6-(−1.8) V at a current density of 200 mA g$^{-1}$ (FIG. 36).
Figure 36:
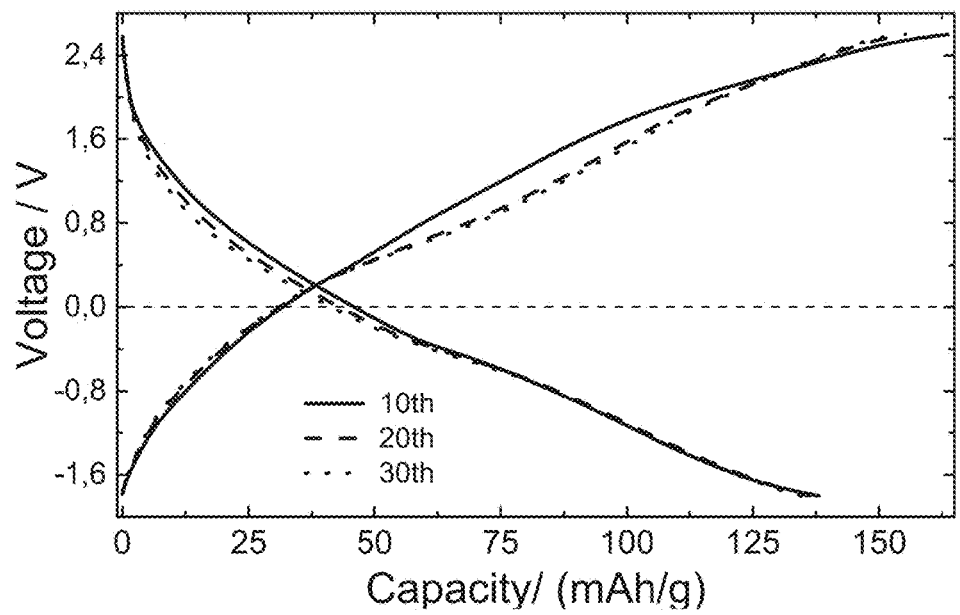

An initial capacity of 72 mAh g$^{-1}$ was achieved in a voltage range of 0.0-2.8 V based on a two-electron redox process between CuDEPP$^{2+}$ and CuDEPP at the cathode and between CuDEPP$^{2-}$ and CuDEPP at the anode, respectively (shown in FIG. 35). Due to the bipolar redox-activity of the CuDEPP molecule (CuDEPP$^{2+}$⇌CuDEPP⇌CuDEPP$^{2-}$), such a symmetric cell can also be operated in a voltage range of 2.6-(−1.8) V as shown in FIG. 36. This proves the four-electron transfer between the CuDEPP$^{2+}$ and CuDEPP$^{2-}$ species.

The invention claimed is:

1. An electrode comprising a compound of general Formula (1):

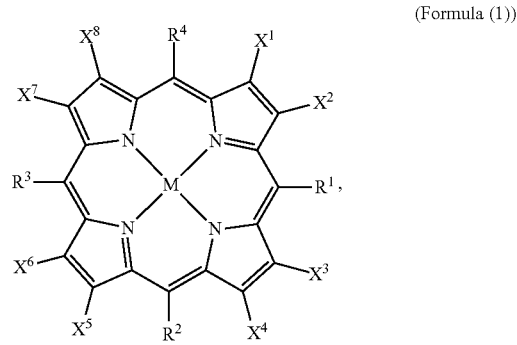

(Formula (1))

wherein M is selected from the group consisting of a transition metal ion, an alkaline earth metal ion, a p-block element ion, and a lanthanide ion, wherein R$^1$ and R$^3$ are each an unsubstituted ethynyl group, wherein R$^2$ and R$^4$ and X$^1$ to X$^8$ are each independently selected from the group consisting of a hydrogen atom, an alkyl group, an alkenyl group, an alkynyl group, an aryl group, a heteroaryl group, a halogen atom, —NZ$^1$Z$^2$, —NO$_2$, —CN, —OZ$^3$, —C(O)Z$^4$, —C(O)NZ$^5$Z$^6$, and —COOZ$^7$, wherein Z$^1$ to Z$^7$ are each independently selected from a hydrogen atom, an alkyl group, an alkenyl group, an alkynyl group, an aryl group, a heteroaryl group, and a halogen atom, and wherein the alkyl groups, the alkenyl groups, the alkynyl groups, the aryl groups, and the heteroaryl groups are each independently substituted or unsubstituted.

2. The electrode according to claim 1, wherein M is Cu(II).

3. The electrode according to claim 1, wherein R$^2$ and R$^4$ are each a phenyl group.

4. The electrode according to claim 1, wherein the compound is [5,15-bis(ethynyl)-10,20-diphenylporphinato]copper(II).

5. The electrode according to claim 4, wherein the content of the compound ranges from 20% to 100%, based on the total weight of the electrode.

6. The electrode according to claim 4, further comprising a binder and/or electrically conductive additives.

7. The electrode according to claim 6, wherein the content of the binder ranges from 0% to 40% and/or the content of the electrically conductive additives ranges from 0% to 80%, based on the total weight of the electrode.

8. The electrode according to claim 6, wherein the binder is selected from the group consisting of polyvinylidene fluoride binder, polyvinylidene fluoride-co-hexafluoropropene (PVDF-HFP), sodium carboxymethyl cellulose (CMC), polyvinylpyrrolidone (PVP), poly(ethyleneoxide) (PEO), polytetrafluorethylene (PTFE), and poly(acrylic acid) (PAA).

9. A battery cell comprising at least one electrode according to claim 4.

10. The battery cell according to claim 9, comprising one electrode as a cathode or as an anode.

11. The battery cell according to claim 9, comprising two electrodes, wherein one of the two electrodes is a cathode and the other electrode is as an anode.

* * * * *